United States Patent
Karo et al.

(10) Patent No.: US 8,498,687 B2
(45) Date of Patent: Jul. 30, 2013

(54) BODY FAT MEASUREMENT DEVICE

(75) Inventors: Hiromichi Karo, Kyoto (JP); Takehiro Hamaguchi, Kyoto (JP); Kazuhisa Tanabe, Kyoto (JP); Yasuaki Murakawa, Kyoto (JP); Tomoya Ijiri, Kameoka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/571,173

(22) Filed: Aug. 9, 2012

(65) Prior Publication Data

US 2012/0310068 A1 Dec. 6, 2012

Related U.S. Application Data

(63) Continuation of application No. PCT/JP2011/052761, filed on Feb. 9, 2011.

(30) Foreign Application Priority Data

Mar. 25, 2010 (JP) .................................. 2010-070373

(51) Int. Cl.
*A61B 5/053* (2006.01)

(52) U.S. Cl.
USPC ........................... 600/382; 600/393; 600/547

(58) Field of Classification Search
USPC ... 600/372, 382, 390, 393, 547, 386; 439/909
See application file for complete search history.

(56) References Cited

U.S. PATENT DOCUMENTS

| 5,785,665 | A | * | 7/1998 | Soejima .................... 600/594 |
| 5,810,742 | A | * | 9/1998 | Pearlman .................... 600/547 |
| 2003/0216665 | A1 | * | 11/2003 | Masuo et al. .................. 600/547 |
| 2004/0077969 | A1 | * | 4/2004 | Onda et al. .................... 600/547 |
| 2005/0222516 | A1 | * | 10/2005 | Kasahara et al. ............. 600/547 |
| 2006/0025701 | A1 | * | 2/2006 | Kasahara .................... 600/547 |
| 2006/0235327 | A1 | * | 10/2006 | Masuo et al. .................. 600/547 |

(Continued)

FOREIGN PATENT DOCUMENTS

| JP | A-2001-252258 | 9/2001 |
| JP | A-2002-369806 | 12/2002 |

(Continued)

OTHER PUBLICATIONS

International Search Report issued in International Patent Application No. PCT/JP2011/052761 dated Apr. 12, 2011.

*Primary Examiner* — Lee S Cohen
*Assistant Examiner* — Erin M Cardinal
(74) *Attorney, Agent, or Firm* — Oliff & Berridge, PLC

(57) ABSTRACT

A body fat measurement device includes: hand electrodes that make contact with both hands; back area electrodes that makes contact with the surface of the back area side of the trunk area; foot electrodes that make contact with both feet; a body impedance measurement unit that measures a body impedance in a body using these multiple electrodes; and a body fat mass calculation unit that calculates a body fat mass based on the body impedance measured by the body impedance measurement unit. The foot electrodes that make contact with both feet are provided on a platform unit in an exposed state, and the hand electrodes that make contact with both hands and the back area electrodes that make contact with the surface of the back area side of the trunk area are all provided on a fitting unit in an exposed state.

6 Claims, 17 Drawing Sheets

U.S. PATENT DOCUMENTS

| | | | |
|---|---|---|---|
| 2007/0038140 A1* | 2/2007 | Masuo et al. | 600/547 |
| 2008/0221476 A1* | 9/2008 | Sakai | 600/547 |
| 2008/0243026 A1* | 10/2008 | Tsuji | 600/547 |
| 2009/0024053 A1* | 1/2009 | Kasahara | 600/547 |
| 2010/0121216 A1* | 5/2010 | Hamaguchi et al. | 600/547 |

FOREIGN PATENT DOCUMENTS

| | | |
|---|---|---|
| JP | A-2005-288023 | 10/2005 |
| JP | A-2007-14664 | 1/2007 |
| JP | A-2007-159702 | 6/2007 |
| JP | A-2008-228890 | 10/2008 |
| JP | A-2008-237571 | 10/2008 |
| JP | A-2010-57543 | 3/2010 |
| WO | WO 2010/024039 A1 | 3/2010 |

\* cited by examiner

BODY FAT MEASUREMENT DEVICE

This is a Continuation of Application No. PCT/JP2011/052761 filed Feb. 9, 2011, which claims priority to Japanese Patent Application No. 2010-070373 filed Mar. 25, 2010. The disclosure of the prior applications is hereby incorporated by reference herein in its entirety.

TECHNICAL FIELD

The present invention relates to body fat measurement devices configured so as to be capable of calculating the body fat mass of a measurement subject by measuring a body impedance, and particularly relates to body fat measurement devices configured so as to be capable of easily measuring a visceral fat mass and/or a subcutaneous fat mass in households or the like.

BACKGROUND ART

In recent years, fat mass is gaining attention as an indicator used to determine the health of a measurement subject. In particular, visceral fat mass is gaining attention as an indicator for determining whether or not a person is suffering from central obesity. Central obesity is said to bring about lifestyle-related diseases that can easily lead to artery hardening, such as diabetes, hypertension, and hyperlipidemia, and the stated indicators hold promise in terms of preventing such diseases. "Visceral fat" refers to fat that accumulates around the internal organs on the inner side of the abdominal muscles and the back muscles, and is distinct from the subcutaneous fat that is located toward the surface of the trunk area. It is typical to employ the surface area occupied by visceral fat in a cross-section of the trunk area that corresponds to the navel (referred to as a "visceral fat cross-sectional area" hereinafter) as an indicator of the visceral fat mass.

Normally, visceral fat mass is measured by analyzing images obtained through X-ray computed tomography (CT), magnetic resonance imaging (MRI), or the like. In such image analysis, the visceral fat cross-sectional area is calculated geometrically from a tomographic image of the trunk area obtained by using X-ray CT, MRI, or the like. However, it is necessary to use several pieces of large equipment installed in a medical facility, such as X-ray CT, MRI, or other machines, in order to make use of such a measurement method; thus it is extremely difficult to measure visceral fat mass on a daily basis through such a measurement method. X-ray CT also poses the problem of exposure to radiation, and thus cannot necessarily be called a desirable measurement method.

A body impedance technique is being considered as an alternative to these measurement methods. The body impedance technique is a method for measuring body fat mass widely used in household-based body fat measurement devices; in this technique, electrodes are placed in contact with the four limbs, the body impedance is measured using those electrodes, and the body fat mass is calculated from the measured body impedance. The stated body fat measurement device makes it possible to accurately measure the extent of body fat buildup throughout the entire body or in specific areas such as the four limbs, the trunk area, or the like.

However, conventional body fat measurement devices that use the body impedance technique measure the extent of body fat buildup throughout the entire body or in specific areas such as the four limbs, the trunk area, or the like, as mentioned earlier, and are not capable of accurately extracting and measuring the extent of visceral fat buildup, the extent of subcutaneous fat buildup, and the like individually. This is because, as mentioned above, conventional body fat measurement devices are configured so that the electrodes are attached only to the four limbs, and thus the visceral fat and subcutaneous fat cannot be accurately measured individually.

Accordingly, bringing electrodes into direct contact with the trunk area, measuring the body impedance using those electrodes, and individually and accurately calculating the visceral fat mass and the subcutaneous fat mass based on that measurement is being considered as a way to solve this problem. For example, JP 2002-369806A discloses a body fat measurement device configured so that electrodes are provided on the inner circumferential surface of a belt member and the belt member is wrapped around and anchored to the trunk area of a measurement subject, thus placing the electrodes in contact with the trunk area.

Meanwhile, JP 2005-288023A and JP 2008-237571A disclose body fat measurement devices configured so that electrodes are provided on the surface of a fitting unit that is fitted to the abdominal area of a measurement subject and the fitting unit is pressed against the abdominal area, thus placing the electrodes in contact with the abdominal area.

Furthermore, JP 2007-14664A discloses a body fat measurement device configured so that the device is divided into a fitting unit that is fitted to the abdominal area of a measurement subject and a platform unit for the measurement subject to stand upon, where abdominal area electrodes are provided on the surface of the fitting unit, hand electrodes are provided on a handle portion of the fitting unit, and foot electrodes are provided on the stated platform unit; the hand electrodes are placed in contact with the measurement subject's palms by the measurement subject gripping the handle portion of the fitting unit, the abdominal area electrodes are placed in contact with the abdominal area by the measurement subject pressing the fitting unit against his or her abdominal area using the hands that grip the handle portion, and the foot electrodes are placed in contact with the soles of the measurement subject's feet by the measurement subject standing upon the platform unit.

In addition, although not discussing a specific device configuration, JP 2008-228890A mentions being able to accurately measure visceral fat mass and subcutaneous fat mass by placing electrodes in contact with a measurement subject's back without placing electrodes in contact with the measurement subject's abdominal area and placing electrodes in contact with the hands and feet of the measurement subject, measuring the body impedance, and calculating the visceral fat mass and the subcutaneous fat mass based on the measured body impedance.

CITATION LIST

Patent Literature

Patent Literature 1: JP 2002-369806A
Patent Literature 2: JP 2005-288023A
Patent Literature 3: JP 2008-237571A
Patent Literature 4: JP 2007-14664A
Patent Literature 5: JP 2008-228890A

SUMMARY OF INVENTION

Technical Problem

Here, in order to realize a body fat measurement device configured to be capable of easily and accurately calculating visceral fat mass and subcutaneous fat mass at home using the body impedance technique, it is extremely important to meet the following two conditions: one, that the measurement can be performed easily through simple operations; and two, that the measurement subject can perform the measurement him/herself without help from an assistant or the like. In light of this, it is unrealistic for the measurement subject to lie face up or face down during the measurement; it is preferable to employ a configuration in which the measurement can be carried out from a standing or seated position. Therefore, employing a measurement position as disclosed in the stated JP 2002-369806A and JP 2007-14664A is favorable in terms of realizing a body fat measurement device for household use.

However, as disclosed in the stated JP 2008-228890A, it is necessary to place electrodes in contact with the measurement subject's back without placing electrodes in contact with the measurement subject's abdominal area and to place electrodes in contact with the hands and feet of the measurement subject in order to calculate the visceral fat mass and the subcutaneous fat mass is a more accurate manner. One of the reasons for this is that the subcutaneous fat that accumulates on the abdominal area side is relatively thinner than the subcutaneous fat that accumulates on the back area side, and thus if the electrodes are placed in contact with the abdominal area, the current that is applied will flow through fat-free areas, which makes it easy for errors to occur.

However, the body fat measurement device disclosed in the stated JP 2002-369806A does not take into consideration placing electrodes in contact with the hands and feet, whereas the body fat measurement device disclosed in the stated JP 2007-14664A does not take into consideration placing electrodes in contact with the back. Thus it is necessary to make some kind of improvement in order to realize a body fat measurement device capable of easily and accurately calculating visceral fat mass and subcutaneous fat mass at home while employing the measurement method disclosed in the stated JP 2008-228890A.

Having been achieved in order to solve the stated problems, it is an object of the present invention to provide a body fat measurement device capable of easily and accurately measuring body fat masses, such as visceral fat mass, even at home.

Solution to Problem

A body fat measurement device according to the present invention includes multiple electrodes, a body impedance measurement unit, a body fat mass calculation unit, and a fitting unit. The multiple electrodes are for making contact with predetermined areas of the surface of a measurement subject's body, and include at least back area electrodes for making contact with the surface of a back area that is an area on the back side of the measurement subject's trunk area and upper limb electrodes for making contact with the surface of the measurement subject's upper limbs. The body impedance measurement unit is a unit that measures a body impedance of the measurement subject's body using the multiple electrodes. The body fat mass calculation unit is a unit that calculates a body fat mass based on the body impedance measured by the body impedance measurement unit. The fitting unit is an element for bringing the back area electrodes into contact with the measurement subject's back area surface in a pressurized state, when the fitting unit is in a fitted state. The back area electrodes and the upper limb electrodes are all provided on the surface of the fitting unit in an exposed state.

In the body fat measurement device according to the present invention, it is preferable for the fitting unit to include a frame member capable of being disposed so as to surround the measurement subject's trunk area when in the fitted state, and in such a case, for the back area electrodes and the upper limb electrodes to all be provided on the surface of the frame member in an exposed state.

In the body fat measurement device according to the present invention, it is preferable for the back area electrodes to be provided on a rear area of the frame member so that the surfaces of the back area electrodes that make contact with the back area surface face forward when in the fitted state, and in such a case, for the upper limb electrodes to be provided on at least one of a front area, a right-side area, and a left-side area that exclude the rear area of the frame member.

In the body fat measurement device according to the present invention, it is preferable for the area of the frame member in which the upper limb electrodes are provided to have a shape that can be gripped by the measurement subject's hands when in the fitted state.

In the body fat measurement device according to the present invention, it is preferable for the fitting unit to include a belt member that can be wrapped around the measurement subject's trunk area when in the fitted state, and in such a case, for the back area electrodes and the upper limb electrodes to be provided on the surface of the belt member in an exposed state.

In the body fat measurement device according to the present invention, it is preferable for the back area electrodes to be provided on a rear area of the inner circumferential surface of the belt member so that the surfaces of the back area electrodes that make contact with the back area surface face forward when in the fitted state, and in such a case, for the upper limb electrodes are provided in positions between the side areas and the front area, excluding the rear area, on the outer circumferential surface of the belt member, so that the surfaces of the upper limb electrodes that make contact with the upper limbs face outward when in the fitted state.

In the body fat measurement device according to the present invention, it is preferable for the areas of the belt member in which the upper limb electrodes are provided to have plate shapes or curved shapes so that the measurement subject's palms can make contact with the upper limb electrodes when in the fitted state by the measurement subject placing his/her palms thereon, without gripping the belt member.

In the body fat measurement device according to the present invention, it is preferable for the multiple electrodes to further include lower limb electrodes for making contact with the surfaces of the measurement subject's lower limbs. In this case, it is preferable for the body fat measurement device according to the present invention to further comprise a platform unit for bringing the lower limb electrodes into contact with the soles of the measurement subject's feet when the measurement subject stands on the platform unit, and in such a case, for the lower limb electrodes to be provided on a top surface of the platform unit in an exposed state. Furthermore, in such a case, it is preferable for the platform unit to include a body weight measurement unit that measures the weight of the measurement subject.

In the body fat measurement device according to the present invention, it is preferable for the multiple electrodes to further include lower limb/hip electrodes for making contact with the surfaces of the measurement subject's lower limbs or hip area. In this case, it is preferable for the fitting unit to include extending unit portions for bringing the lower limb/hip electrodes into contact with the surfaces of the lower limbs or hip area by being pulled out from the fitting unit via connection lines, and in such a case, for the lower limb/hip electrodes to be provided on the surfaces of the extending unit portions in an exposed state.

In the body fat measurement device according to the present invention, it is preferable for the body fat mass calculation unit to include at least one of a visceral fat mass calculation unit that calculates the visceral fat mass of the measurement subject and a subcutaneous fat mass calculation unit that calculates the subcutaneous fat mass of the measurement subject.

Advantageous Effects of Invention

According to the present invention, a body fat measurement device capable of measuring a body fat mass such as a visceral fat mass easily and accurately in a household or the like can be provided.

DESCRIPTION OF EMBODIMENTS

Figure 1A:
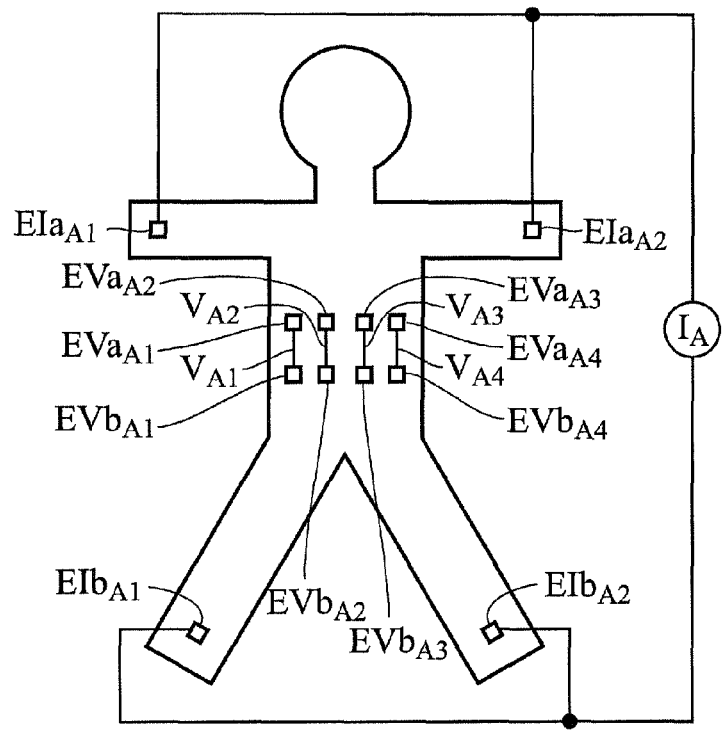
FIG. 1A is a diagram illustrating the fundamentals of measurement performed by a body fat measurement device according to a first embodiment of the present invention.

Hereinafter, embodiments of the present invention will be described in detail with reference to the drawings. Note that in the following embodiments, identical or corresponding elements are given the same reference numerals in the drawings, and individual descriptions thereof will not be repeated.

Before describing the various embodiments of the present invention, definitions will first be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. Finally, "body axis" refers to an axis located along the direction in which the trunk area extends, or in other words, an axis extending in a direction approximately perpendicular to a side cross-section of the measurement subject's trunk area.

First Embodiment

Figure 1B:
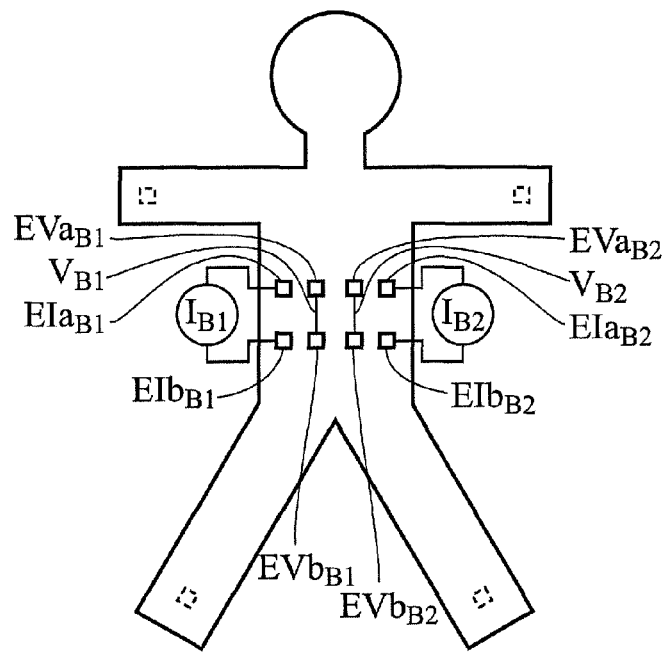
FIG. 1B is a diagram illustrating the fundamentals of measurement performed by the body fat measurement device according to the first embodiment of the present invention.

FIGS. 1A and 1B are diagrams illustrating the fundamentals of measurement performed by a body fat measurement device according to a first embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 1A and 1B. Note that FIGS. 1A and 1B both illustrate the measurement subject from the back side thereof.

As shown in FIG. 1A, electrodes $EIa_{A1}$ and $EIa_{A2}$ are attached to the surface of the left hand of the measurement subject and the surface of the right hand of the measurement subject, respectively, in order to obtain the body impedance for the entire trunk area. Likewise, electrodes $EIb_{A1}$ and $EIb_{A2}$ are attached to the surface of the left foot of the measurement subject and the surface of the right foot of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A, a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

In this state, a constant current $I_A$ that passes through the trunk area is applied to the measurement subject using the electrodes $EIa_{A1}$, $EIa_{A2}$, $EIb_{A1}$, and $EIb_{A2}$ attached to both hands and both feet, respectively. While the constant current $I_A$ is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current $I_A$ is flowing between both hands and both feet, which are positioned at a distance from the trunk area, and thus almost all of the applied constant current $I_A$ passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current $I_A$ is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in FIG. 1B, a total of eight electrodes, or electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

In this state, a constant current $I_{B1}$ that passes through the back area locally is applied to the measurement subject using the pair of electrodes $EIa_{B1}$ and $EIb_{B1}$, and a constant current $I_{B2}$ that passes through the back area locally is applied to the measurement subject using the pair of electrodes $EIa_{B2}$ and $EIb_{B2}$. While the constant currents $I_{B1}$ and $I_{B2}$ are applied, a potential difference $V_{B1}$ is detected using the pair of electrodes $EVa_{B1}$ and $EVb_{B1}$ attached to the back area surface, and a potential difference $V_{B2}$ is detected using the pair of electrodes $EVa_{B2}$ and $EVb_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential differences $V_{B1}$ and $V_{B2}$ calculated in this manner. Note that if the body impedance Zs is found at this time by calculating the average value of the two stated potential differences $V_{B1}$ and $V_{B2}$, it is possible to reduce the influence of variations in the fat distribution within the surface layer area in the back area of the trunk area. Note that potential differences can also be calculated in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B1}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \qquad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as $2a$ and the depth of the trunk area is taken as $2b$, and because the trunk area has a generally oval cross-sectional shape, the trunk area cross-sectional area St can be approximated through the following Formula (2).

$$St = \pi \times a \times b \qquad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient α for reducing error. This coefficient αa is obtained, for example, by finding the optimum value for a that fulfills St'=α×π×a×b, from the relationship between the stated a and b and a trunk area cross-sectional area St' obtained from a sample of a large number of X-ray CT images.

Accordingly, the stated Formula (2) can approximate with a lower degree of error through the following Formula (3) by using the coefficient α.

$$St = \alpha \times \pi \times a \times b \qquad \text{Formula (3)}$$

Note that it is preferable to optimize the coefficient α multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient α in accordance with the measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa=\beta \times a \times (1/Zt) \qquad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, β represents a coefficient for converting the body impedance Zt of the entire trunk area into the non-fat cross-sectional area Sa, and an optimum value can be found, for example, based on a sample of a large number of X-ray CT images, in the same manner as when finding the coefficient α. In other words, the optimum value for β that fulfils $Sa'=\beta \times a \times (1/Zt)$ can be found from the relationship between a non-fat cross-sectional area Sa' obtained from a sample of a large number of X-ray CT images, the body impedance Zt of the entire trunk area of the measurement subject imaged by the X-ray CT, and the stated a.

Note that it is preferable for the stated coefficient β to be optimized as appropriate in accordance with the measurement subject information, in the same manner as the coefficient α mentioned above. In other words, the non-fat cross-sectional area Sa can be approximated with a higher degree of accuracy by changing the value of the stated coefficient β in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb=\gamma \times a \times Zs \qquad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, γ represents a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient α or the coefficient β. In other words, the optimum value for γ that fulfils $Sb'=\gamma \times a \times Zs$ can be found from the relationship between a subcutaneous fat cross-sectional area Sb∝ obtained from a sample of a large number of X-ray CT images, the body impedance Zs of the surface layer area on the back area side of the trunk area of the measurement subject imaged by the X-ray CT, and the stated a.

Note that it is preferable for the stated coefficient γ to be optimized as appropriate in accordance with the measurement subject information, in the same manner as the coefficient α and the coefficient β mentioned above. In other words, the subcutaneous fat cross-sectional area Sb can be approximated with a higher degree of accuracy by changing the value of the stated coefficient γ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx=\alpha \times \pi \times a \times b - \beta \times a \times (1/Zt) - \gamma \times a \times Zs \qquad \text{Formula (6)}$$

Figure 2:
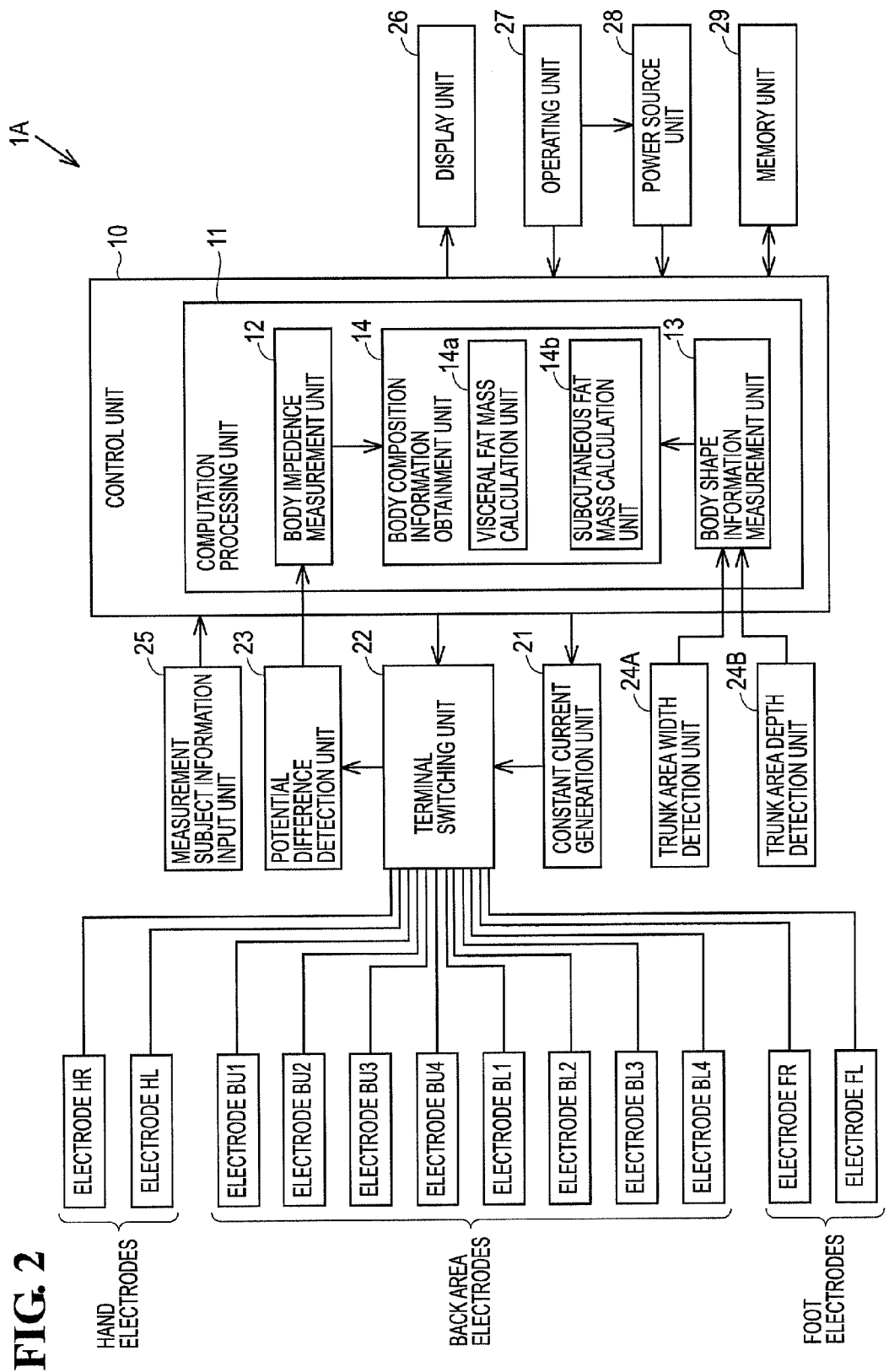
FIG. 2 is a diagram illustrating the functional block configuration of the body fat measurement device according to the first embodiment of the present invention.

FIG. 2 is a diagram illustrating the functional block configuration of the body fat measurement device according to the present embodiment. Next, the functional block configuration of the body fat measurement device according to the present embodiment will be described with reference to FIG. 2.

As shown in FIG. 2, a body fat measurement device 1A according to the present embodiment primarily includes: a control unit 10; a constant current generation unit 21; a terminal switching unit 22; a potential difference detection unit 23; a trunk area width detection unit 24A; a trunk area depth detection unit 24B; a measurement subject information input unit 25; a display unit 26; an operating unit 27; a power source unit 28; a memory unit 29; and multiple electrodes HR, HL, BU1-BU4, BL1-BL4, FR, and FL that are fitted to the body of the measurement subject. The control unit 10 includes a computation processing unit 11, and the computation processing unit 11 has a body impedance measurement unit 12, a body shape information measurement unit 13, and a body composition information obtainment unit 14.

The control unit 10 is configured of, for example, a CPU (Central Processor Unit), and is a unit for controlling the body fat measurement device 1A as a whole. Specifically, the control unit 10 outputs instructions to the various aforementioned functional blocks, accepts inputs of various types of information from the various aforementioned functional blocks, performs various types of computation processes based on the various types of information accepted, and so on. The various types of computation processes are carried out by the stated computation processing unit 11 provided in the control unit 10.

The aforementioned multiple electrodes include: hand electrodes HR and HL serving as upper limb electrodes placed in contact with surfaces of the upper limbs of the measurement subject; back area electrodes BU1-BU4 and BL1-BL4 placed in contact with the back area surface of the measurement subject; and foot electrodes FR and FL serving as lower limb electrodes placed in contact with surfaces of the lower limbs of the measurement subject. Of these, the hand electrodes HR and HL are placed in contact with the measurement subject's palms, whereas the foot electrodes FR and FL are placed in contact with the soles of the measurement subject's feet. Meanwhile, as shown in FIGS. 1A and 1B, the back area electrodes BU1-BU4 and BL1-BL4 are arranged in rows and placed in contact with the back area surface of the measurement subject. Note that the hand electrodes HR and HL, back area electrodes BU1-BU4 and BL1-BL4, and foot electrodes FR and FL are all electrically connected to the aforementioned terminal switching unit 22.

The terminal switching unit 22 is configured of, for example, a relay circuit; based on instructions inputted from the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit 22 operating based on instructions inputted from the control unit 10, the respective multiple electrodes HR, HL, BU1-BU4, BL1-BL4, FR, and FL function as the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A and the respective electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$ shown in FIG. 1B.

The constant current generation unit 21 generates a constant current based on an instruction inputted from the control unit 10, and supplies the generated constant current to the stated constant current application electrodes via the terminal switching unit 22. A high-frequency current (for example, 50 kHz, 500 μA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the control unit 10. Through this, the potential difference between the potential difference detection electrodes is detected in a state in which the aforementioned constant current is applied to the measurement subject.

The trunk area width detection unit 24A is a detection unit for measuring the width of the measurement subject's trunk area without making contact therewith, and is configured of, for example, a range sensor such as an optical sensor. Meanwhile, the trunk area depth detection unit 24B is a detection unit for measuring the depth of the measurement subject's trunk area without making contact therewith, and is configured of, for example, a range sensor such as an optical sensor. The trunk area width detection unit 24A and the trunk area depth detection unit 24B output signals based on the values detected to the body shape information measurement unit 13. In addition to the stated optical sensors, it should be noted that various types of non-contact range sensors that use ultrasound waves or electromagnetic waves (light of various wavelength ranges including laser light, visible light, and so on, radio waves, magnetism, electrical fields, and the like) can also be used as the trunk area width detection unit 24A and the trunk area depth detection unit 24B; contact-type range sensors can also be used.

The measurement subject information input unit 25 is a unit for obtaining information regarding the measurement subject used in computation processes carried out by the computation processing unit 11, and is configured of for example, keys and the like that can be depressed by the measurement subject. Here, the measurement subject information includes at least one of the sex, age, height, weight, and so on of the measurement subject, as mentioned above. The measurement subject information input unit 25 accepts the input of measurement subject information, and outputs the accepted measurement subject information to the control unit 10. Note that the measurement subject information input unit 25 is not absolutely necessary in the configuration of the present invention, and whether or not to provide the measurement subject information input unit 25 can be determined based on whether or not it is necessary to use the measurement subject information in the computation processes performed by the computation processing unit 11. It is also possible to employ a configuration in which, instead of providing the trunk area width detection unit 24A and the trunk area depth detection unit 24B and actually measuring the width and depth of the trunk area, the circumferential length of the trunk area and so on are inputted via the measurement subject information input unit 25 and computations are carried out by a computation processing unit using that information.

The computation processing unit 11 includes the body impedance measurement unit 12, the body shape information measurement unit 13, and the body composition information obtainment unit 14, as mentioned above. Meanwhile, the body composition information obtainment unit 14 includes a visceral fat mass calculation unit 14a and a subcutaneous fat mass calculation unit 14b. The body impedance measurement unit 12 calculates the body impedance based on a signal inputted from the potential difference detection unit 23, and outputs that body impedance to the body composition information obtainment unit 14. The body shape information measurement unit 13 calculates the width and the depth of the measurement subject's trunk area based on the signals inputted from the trunk area width detection unit 24A and the trunk area depth detection unit 24B, and outputs the calculated information to the body composition information obtainment unit 14. The body composition information obtainment unit 14 calculates and obtains the body composition information based on the body impedance inputted from the body impedance measurement unit 12, the width and depth of the trunk area inputted from the body shape information measurement unit 13, and in some cases, the measurement subject information inputted from the measurement subject information input unit 25 as well. More specifically, the visceral fat mass calculation unit 14a calculates a visceral fat mass and the subcutaneous fat mass calculation unit 14b calculates a subcutaneous fat mass.

The display unit 26 is configured of, for example, an LCD (Liquid Crystal Display) or the like, and displays the body composition information calculated by the body composition information obtainment unit 14 as mentioned above. More specifically, the visceral fat mass calculated by the visceral fat mass calculation unit 14a and the subcutaneous fat mass calculated by the subcutaneous fat mass calculation unit 14b are displayed in the display unit 26 based on signals outputted from the control unit 10. Here, with the body fat measurement device 1A according to the present embodiment, the visceral fat mass is displayed as, for example, the visceral fat cross-sectional area, and the subcutaneous fat mass is displayed as, for example, the subcutaneous fat cross-sectional area.

The operating unit 27 is a unit through which the measurement subject inputs commands to the body fat measurement device 1A, and is configured of, for example, buttons and the like that can be depressed by the measurement subject. Note that the operating unit 27 includes various types of operation buttons such as a power button, a measure button, and so on.

The power source unit 28 is a unit for supplying electrical power to the control unit 10, and uses an internal power source such as a battery, an external power source such as an AC outlet, or the like.

The memory unit 29 is configured of, for example, a random access memory (RAM) or a read-only memory (ROM), and is a unit for storing various types of data, programs, and the like for the body fat measurement device 1A. The memory unit 29 stores, for example, the aforementioned measurement subject information, the calculated body composition information, a body composition information measurement program for executing a body composition information measurement process (mentioned later), and so on.

Figure 3:
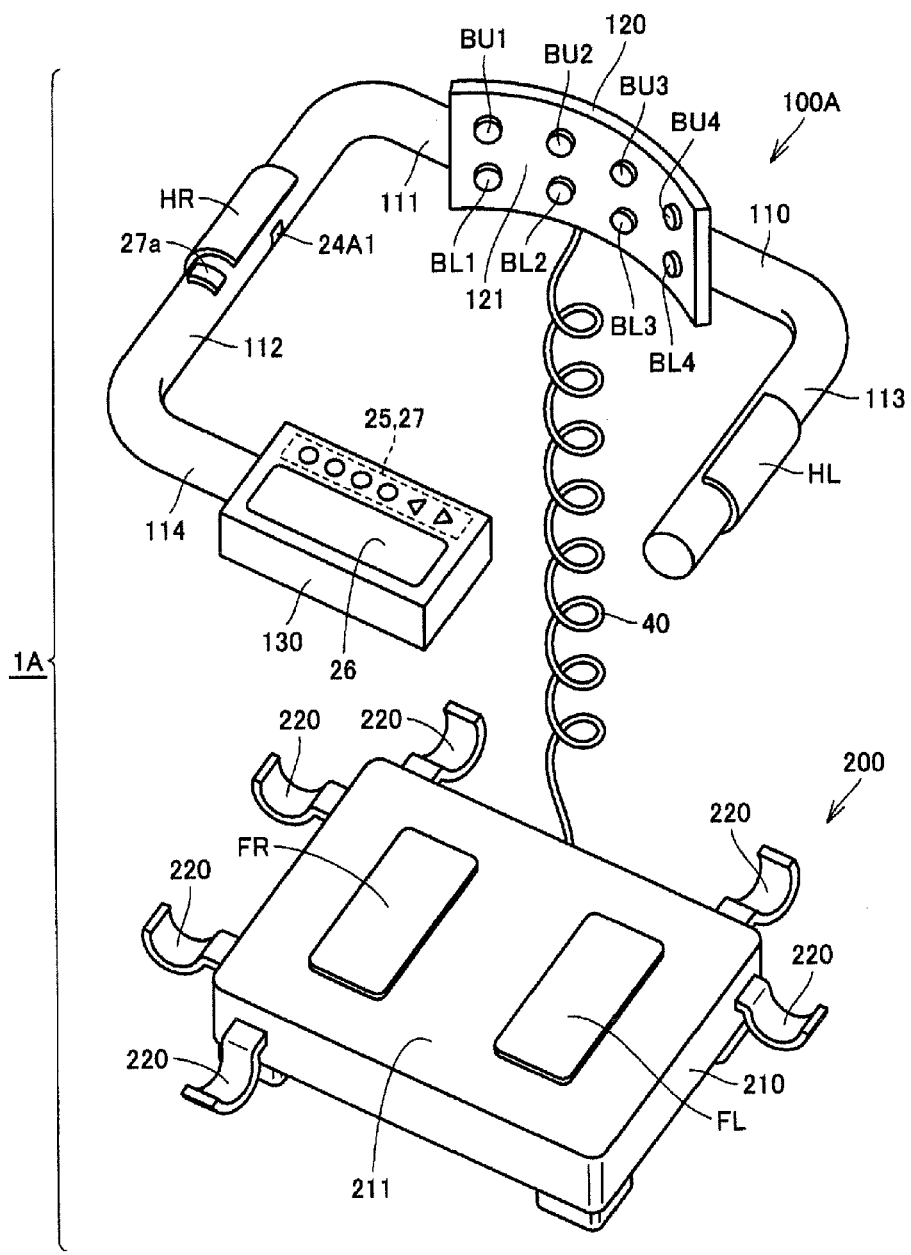
FIG. 3 is a perspective view illustrating the body fat measurement device according to the first embodiment of the present invention in an unstored state.
Figure 4:
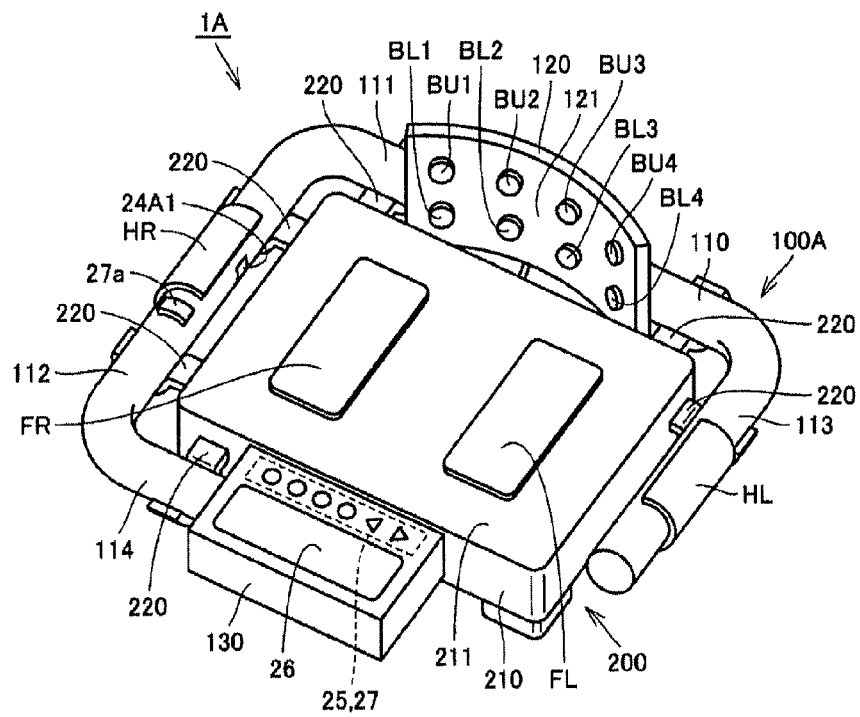
FIG. 4 is a perspective view illustrating the body fat measurement device according to the first embodiment of the present invention in a stored state.
Figure 5:
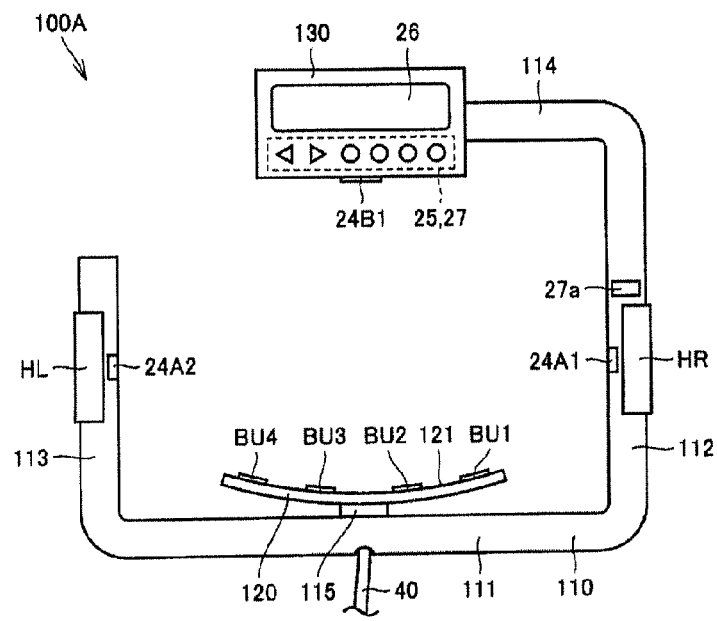
FIG. 5 is a top view of a fitting unit of the body fat measurement device according to the first embodiment of the present invention.

FIG. 3 is a perspective view illustrating the body fat measurement device according to the present embodiment in an unstored state, whereas FIG. 4 is a perspective view illustrating the body fat measurement device in a stored state. FIG. 5, meanwhile, is a top view of a fitting unit shown in FIGS. 3 and 4. Next, the structure of the body fat measurement device according to the present embodiment will be described in detail with reference to FIGS. 3 through 5.

As shown in FIGS. 3 and 4, the body fat measurement device 1A according to the present embodiment includes a fitting unit 100A and a platform unit 200. The fitting unit 100A has a frame shape capable of being disposed so as to surround the trunk area of the measurement subject in a fitted state, which will be described later. Meanwhile, the platform unit 200 is shaped as a platform on which the measurement subject can stand. Note that the fitting unit 100A and the platform unit 200 are connected by a connection cable 40 that electrically connects electrical circuitry provided therein.

As shown in FIGS. 3 through 5, the fitting unit 100A includes: a frame member 110 that includes a rod-shaped rear frame portion 111, a rod-shaped right-side frame portion 112, a rod-shaped left-side frame portion 113, and a rod-shaped front frame portion 114; an electrode support member 120 attached to the rear frame portion 111 of the frame member 110; and a display unit portion 130 attached to the front frame portion 114 of the frame member 110.

The frame member 110 has a frame-shaped outer shape that is approximately rectangular when viewed from above, and has a hollow opening area into which the measurement subject can enter (in other words, into which the measurement subject can insert his/her trunk area). The hollow opening area is defined by the stated rear frame portion 111, right-side frame portion 112, left-side frame portion 113, and front frame portion 114. Note that the left-side frame portion 113 and the front frame portion 114 are not connected, and the aforementioned display unit portion 130 is attached to the end of the front frame portion 114 that is adjacent to the unconnected area.

The electrode support member 120 is disposed in approximately the center of the rear frame portion 111 of the frame member 110 so as to protrude inward. The electrode support member 120 is configured of a curved plate that is bent so that both ends thereof are positioned forward and the center thereof is positioned rearward. The aforementioned back area electrodes BU1-BU4 and BL1-BL4 are provided so as to be exposed on a front surface 121 of the electrode support member 120, and preferably, the back area electrodes BU1-BU4 and BL1-BL4 protrude slightly from the front surface 121 of the electrode support member 120. Here, the electrode support member 120 is positioned and attached on the front surface of the rear frame portion 111 so that surfaces of the back area electrodes BU1-BU4 and BL1-BL4 that make contact with the back area surface of the measurement subject face forward during the fitted state, which will be mentioned later.

Meanwhile, as shown in FIG. 5, the electrode support member 120 is attached to the rear frame portion 111 of the frame member 110 via a connection portion 115 including, for example, a ball joint. Through this, the electrode support member 120 is supported by the rear frame portion 111 in a pivotable state. Note that it is preferable for the direction of the pivoting to be limited so that the electrode support member 120 can pivot only to the left and right in the horizontal plane. Employing such a configuration makes it possible to bring the back area electrodes BU1-BU4 and BL1-BL4 provided on the front surface 121 of the electrode support member 120 into contact with the back area of the measurement subject with certainty and with an appropriate pressure during the fitted state, which will be mentioned later.

Alternatively, the connection portion 115 may be provided with an elastic member such as a spring, and configured so that the electrode support member 120 is elastically supported on the rear frame portion 111. Employing such a configuration makes it possible to bring the back area electrodes BU1-BU4 and BL1-BL4 provided on the front surface 121 of the electrode support member 120 into contact with the back area of the measurement subject with more certainty and with a more appropriate pressure during the fitted state, which will be mentioned later.

As shown in FIGS. 3 through 5, the aforementioned hand electrode HR is provided in approximately the center of the right-side frame portion 112 of the frame member 110. The hand electrode HR is positioned so as to be exposed on the surface of the right-side frame portion 112 of the frame member 110. Meanwhile, the area of the right-side frame portion 112 of the frame member 110 in which the hand electrode HR is provided is formed in a rod shape, so as to be capable of being gripped by the measurement subject's right hand. Here, it is preferable for the surface of the hand electrode HR that makes contact with the palm of the measurement subject's right hand to be disposed so as to mainly face outward from the frame member 110.

Meanwhile, an optical sensor, serving as the aforementioned trunk area width detection unit 24A, is embedded inside approximately the center of the right-side frame portion 112 of the frame member 110, and a detection window portion 24A1 is provided on the inner side of the right-side frame portion 112 in the area in which the optical sensor is embedded. The detection window portion 24A1 is configured of a member that allows light emitted from the optical sensor to pass through.

Furthermore, a measure button 27a is provided in a predetermined location of the right-side frame portion 112 of the frame member 110. Preferably, the measure button 27a is provided in a location adjacent to the hand electrode HR. As a result, it is not necessary for the measurement subject to move his/her right hand during measurement, which makes it possible to provide superior operability.

The aforementioned hand electrode HL is provided in approximately the center of the left-side frame portion 113 of the frame member 110. The hand electrode HL is positioned so as to be exposed on the surface of the left-side frame portion 113 of the frame member 110. Meanwhile, the area of the left-side frame portion 113 of the frame member 110 in which the hand electrode HL is provided is formed in a rod shape, so as to be capable of being gripped by the measurement subject's left hand. Here, it is preferable for the surface of the hand electrode HL that makes contact with the palm of the measurement subject's left hand to be disposed so as to mainly face outward from the frame member 110.

Meanwhile, as shown in FIG. 5, an optical sensor, serving as the aforementioned trunk area width detection unit 24A, is embedded inside approximately the center of the left-side frame portion 113 of the frame member 110, and a detection window portion 24A2 is provided on the inner side of the left-side frame portion 113 in the area in which the optical sensor is embedded. The detection window portion 24A2 is configured of a member that allows light emitted from the optical sensor to pass through.

As shown in FIGS. 3 through 5, the aforementioned display unit portion 130 is attached to the front frame portion 114 of the frame member 110. The display unit 26 is provided on the top surface of the display unit portion 130, and furthermore, the operating unit 27, excluding the measurement subject information input unit 25 and the measure button 27a, is provided on an area of the top surface of the display unit portion 130 that is adjacent to the display unit 26. Note that it is preferable for the display unit portion 130 to be located in front of the measurement subject during the fitted state, and for this reason, the display unit portion 130 is disposed forward from the aforementioned electrode support member 120 (that is, in approximately the center of the horizontal direction of the frame member 110).

Meanwhile, as shown in FIG. 5, an optical sensor, serving as the aforementioned trunk area depth detection unit 24B, is embedded inside the display unit portion 130, and a detection window portion 24B1 is provided on the rear surface side of the display unit portion 130 in the area in which the optical sensor is embedded. The detection window portion 24B1 is configured of a member that allows light emitted from the optical sensor to pass through.

Meanwhile, as shown in FIGS. 3 and 4, the platform unit 200 includes a box-shaped platform portion 210, and support portions 220 that protrude outward from predetermined locations on the front surface, the rear surface, the right-side surface, and the left-side surface of the platform portion 210.

The platform portion 210 has a top surface 211 on which the measurement subject stands, and the aforementioned foot electrodes FR and FL are respectively provided in predetermined locations of the top surface 211. The foot electrodes FR and FL are positioned so as to be exposed on the top surface of the platform portion 210. Here, the configuration is such that the contact surfaces of the foot electrodes FR and FL that make contact with the sole of the measurement subject's right foot and the sole of the measurement subject's left foot are both facing upward.

As shown in FIG. 4, the support portions 220 are units for supporting and storing the fitting unit 100A during the stored state, and have shapes that are capable of accepting and supporting the rear frame portion 111, the right-side frame portion 112, the left-side frame portion 113, and the front frame portion 114, respectively, of the frame member 110. As shown in FIG. 4, during the stored state, the frame member 110 of the fitting unit 100A is placed so as to surround the platform portion 210 of the platform unit 200. Note that in the stored state, it is preferable for the configuration to be such that the connection cable 40 that connects the fitting unit 100A to the platform unit 200 is contained within the platform unit 200. To achieve such a configuration, a reel member capable of taking up the connection cable 40 into the interior of the platform unit 200 may be provided.

The aforementioned control unit 10, constant current generation unit 21, terminal switching unit 22, potential difference detection unit 23, memory unit 29, and so on shown in FIG. 2 may be provided within the fitting unit 100A, or may be provided within the platform portion 210. Furthermore, although the measurement subject information input unit 25, the display unit 26, and operating unit 27 are provided in the fitting unit 100A of the body fat measurement device 1A according to the present embodiment, those units may be provided within the platform unit 200.

Figure 6:
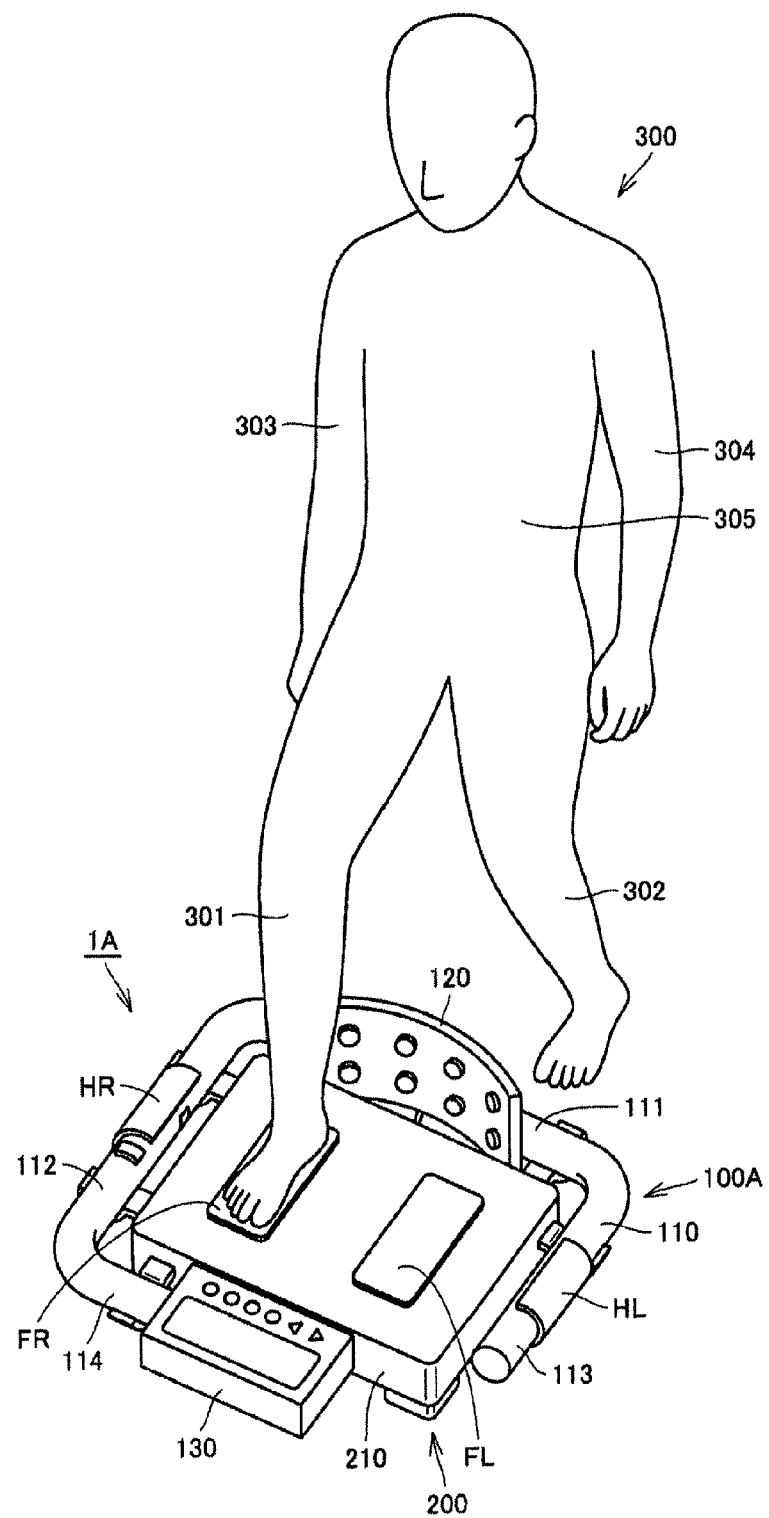
FIG. 6 is a diagram illustrating a procedure to be performed by a measurement subject when carrying out a measurement using the body fat measurement device according to the first embodiment of the present invention.
Figure 7:
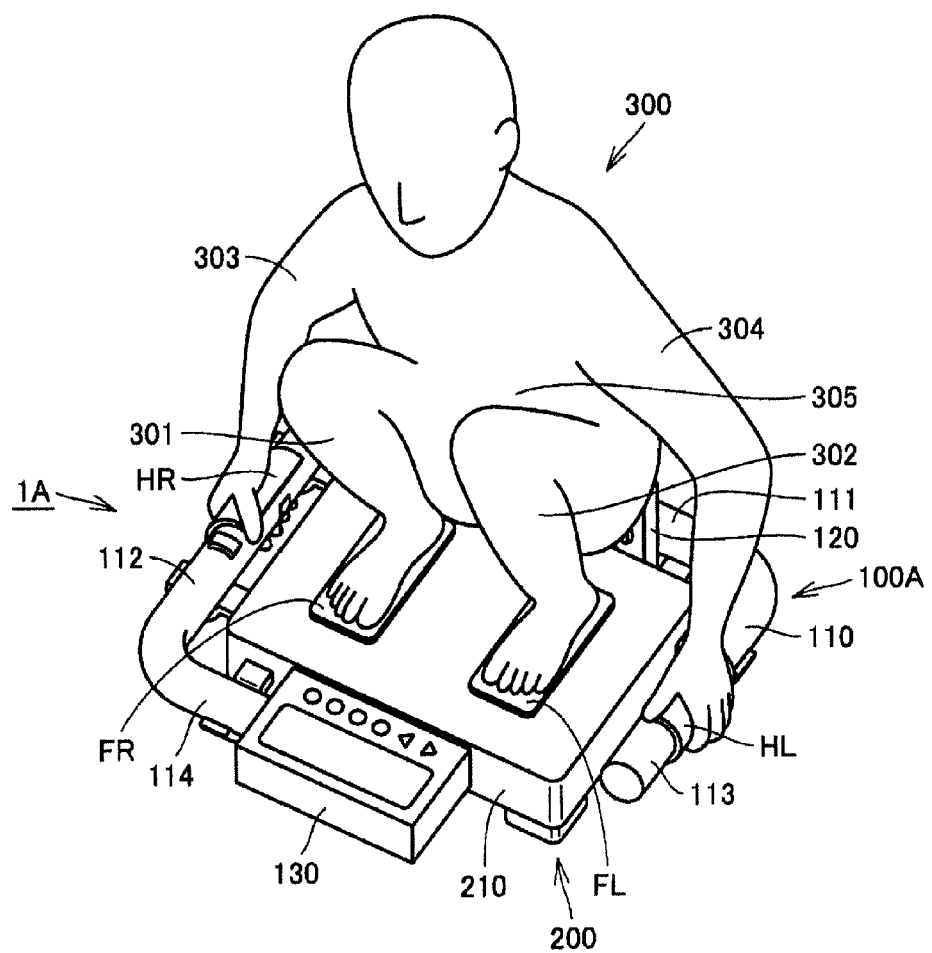
FIG. 7 is a diagram illustrating a procedure to be performed by a measurement subject when carrying out a measurement using the body fat measurement device according to the first embodiment of the present invention.
Figure 8:
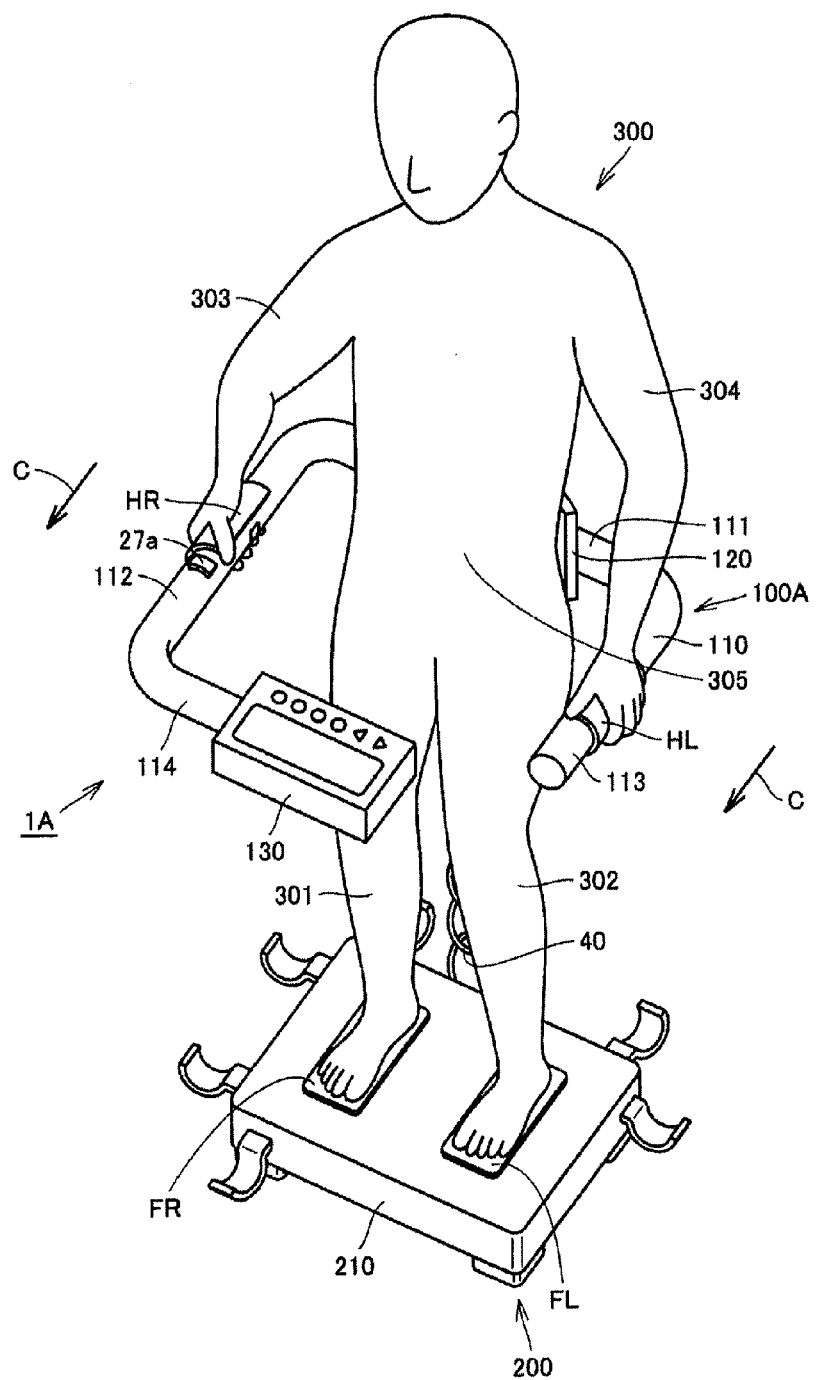
FIG. 8 is a diagram illustrating a procedure to be performed by a measurement subject when carrying out a measurement using the body fat measurement device according to the first embodiment of the present invention.
Figure 9:
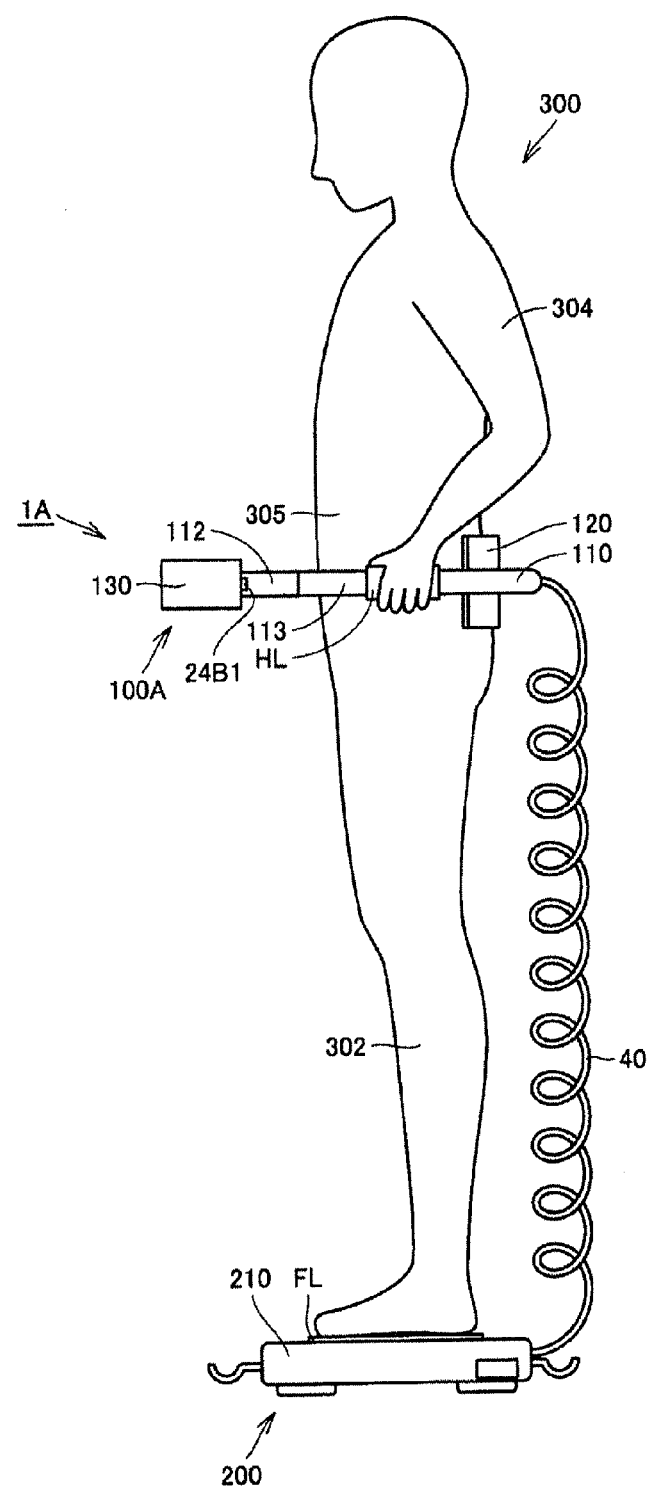
FIG. 9 is a diagram illustrating a fitted state of the fitting unit of the body fat measurement device according to the first embodiment of the present invention.
Figure 10:
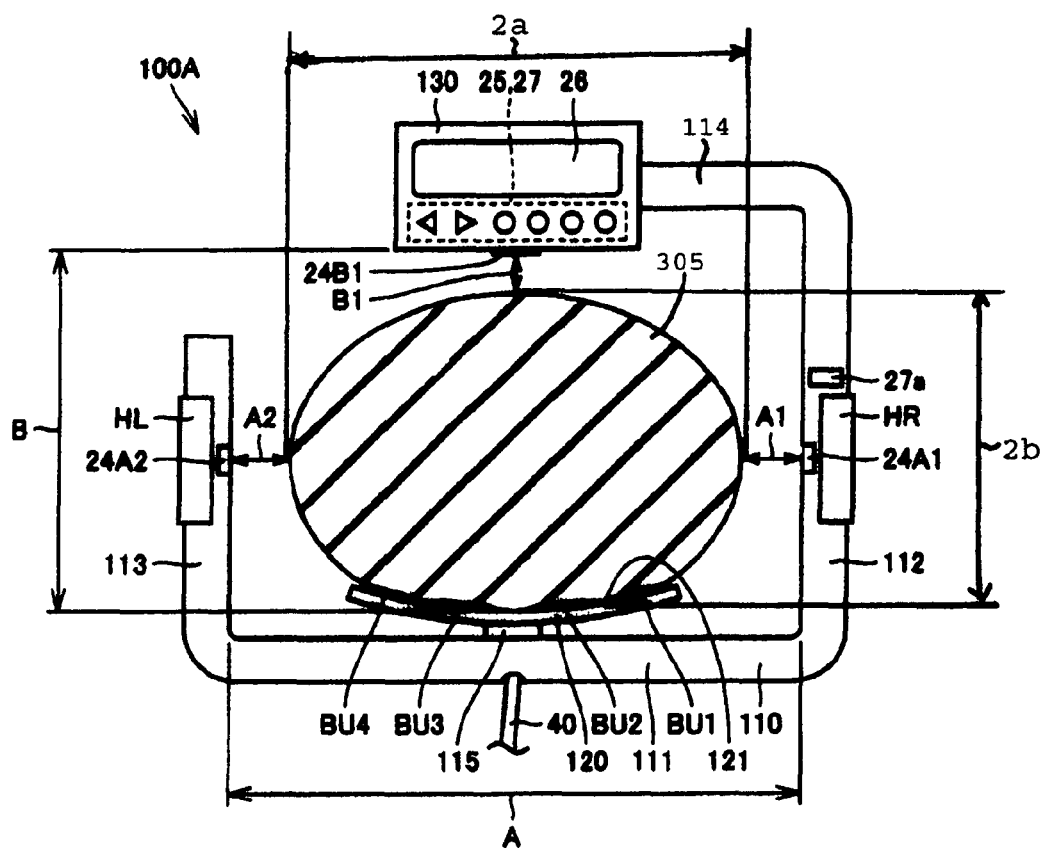
FIG. 10 is a diagram illustrating a fitted state of the fitting unit of the body fat measurement device according to the first embodiment of the present invention.

FIGS. 6 through 8 are diagrams illustrating a procedure to be performed by the measurement subject when carrying out a measurement using the body fat measurement device according to the present embodiment. Meanwhile, FIGS. 9 and 10 are diagrams illustrating the fitting unit of the body fat measurement device according to the present embodiment in the fitted state. Next, a procedure to be performed by the measurement subject and the fitted state of the fitting unit when carrying out measurement using the body fat measurement device according to the present embodiment will be described with reference to FIGS. 6 through 10.

As shown in FIG. 6, when measuring body fat mass using the body fat measurement device 1A according to the present embodiment, first, a measurement subject 300 stands upon the platform unit 200 of the body fat measurement device 1A in the stored state. At this time, the measurement subject 300 brings the sole of his/her right foot 301 into contact with the foot electrode FR provided on the platform unit 200, and brings the sole of his/her left foot 302 into contact with the foot electrode FL provided on the platform unit 200.

Next, as shown in FIG. 7, the measurement subject 300 bends his/her upper body and assumes a squatting position, and grips the right-side frame portion 112 of the fitting unit 100A with his/her right hand 303 and the left-side frame portion 113 of the fitting unit 100A with his/her left hand 304. At this time, the measurement subject 300 brings the palm of his/her right hand 303 into contact with the hand electrode HR provided in the fitting unit 100A, and brings the palm of his/her left hand 304 into contact with the hand electrode HL provided in the fitting unit 100A.

Next, as shown in FIG. 8, the measurement subject 300 straightens his/her upper body while gripping the fitting unit 100A, and assumes a standing position. As this time, the measurement subject 300 does not change his/her foot placement, keeping the sole of his/her right foot 301 in contact with the foot electrode FR and the sole of his/her left foot 302 in contact with the foot electrode FL. Here, the measurement subject 300 lifts the fitting unit 100A by straightening his/her body, and the trunk area 305 of the measurement subject 300 is then positioned in the hollow opening area of the fitting unit 100A, surrounded by the frame member 110. Note that the connection cable 40 is pulled from the platform unit 200 when the fitting unit 100A is lifted.

Next, the measurement subject 300 adjusts the position of the fitting unit 100A by moving the fitting unit 100A in the direction of an arrow C in FIG. 8 while continuing to grip the fitting unit 100A, so that the front surface 121 of the electrode support member 120 provided in the fitting unit 100A is pressed against the back area surface (more specifically, against the surface of his/her hips on the back side). Note that at this time, the measurement subject 300 takes care so that the frame member 110 of the fitting unit 100A is positioned horizontally.

As a result, the fitting unit 100A enters the fitted state shown in FIGS. 9 and 10, and the measurement of body fat mass can be started. Here, in order to start the measurement of the body fat mass, the measurement subject 300 may depress the measure button 27a using the thumb of his/her right hand 303. Although descriptions have been omitted above, the measurement subject 300 is required to press the power button at an appropriate timing. Although the timing at which the power button is pressed is not particularly limited, it is preferable for the power button to be pressed before the measurement subject 300 assumes a squatting position and grips the fitting unit 100A.

As shown in FIGS. 9 and 10, in the fitted state, where the fitting unit 100A is fitted to the measurement subject 300, the optical sensors serving as the trunk area width detection unit 24A and the optical sensor serving as the trunk area depth detection unit 24B are positioned around the trunk area 305 in a position including the location of the navel of the measurement subject 300. Accordingly, the light emitted from the pair of optical sensors serving as the trunk area width detection unit 24A can irradiate the right side surface of the trunk area 305 of the measurement subject 300 (in other words, the surface of the right flank) and the left side surface of the trunk area 305 (in other words, the surface of the left flank) through the detection window portions 24A1 and 24A2, and the light emitted from the optical sensor serving as the trunk area depth detection unit 24B can irradiate the front surface of the trunk area 305 of the measurement subject 300 (in other words, the vicinity of the location of the navel in the abdominal area) through the detection window portion 24B1.

Here, as shown in FIG. 10, a width 2a of the trunk area 305 of the measurement subject 300 can be calculated using a distance A1 (that is, the distance between the right-side frame portion 112 and the right side surface of the trunk area 305 of the measurement subject 300) and a distance A2 (that is, the distance between the left-side frame portion 113 and the left side surface of the trunk area 305 of the measurement subject 300) detected by the pair of optical sensors serving as the trunk area width detection unit 24A, along with a predetermined distance A (that is, the distance between the right-side frame portion 112 and the left-side frame portion 113). Likewise, a depth 2b of the trunk area 305 of the measurement subject 300 can be calculated using a distance B1 detected by the optical sensor serving as the trunk area depth detection unit 24B (that is, the distance between the rear surface of the display unit portion 130 and the front surface of the trunk area 305 of the measurement subject 300) and a predetermined distance B (that is, the distance between the rear surface of the display unit portion 130 and the center of the front surface 121 of the electrode support member 120 in the horizontal direction).

Figure 11:
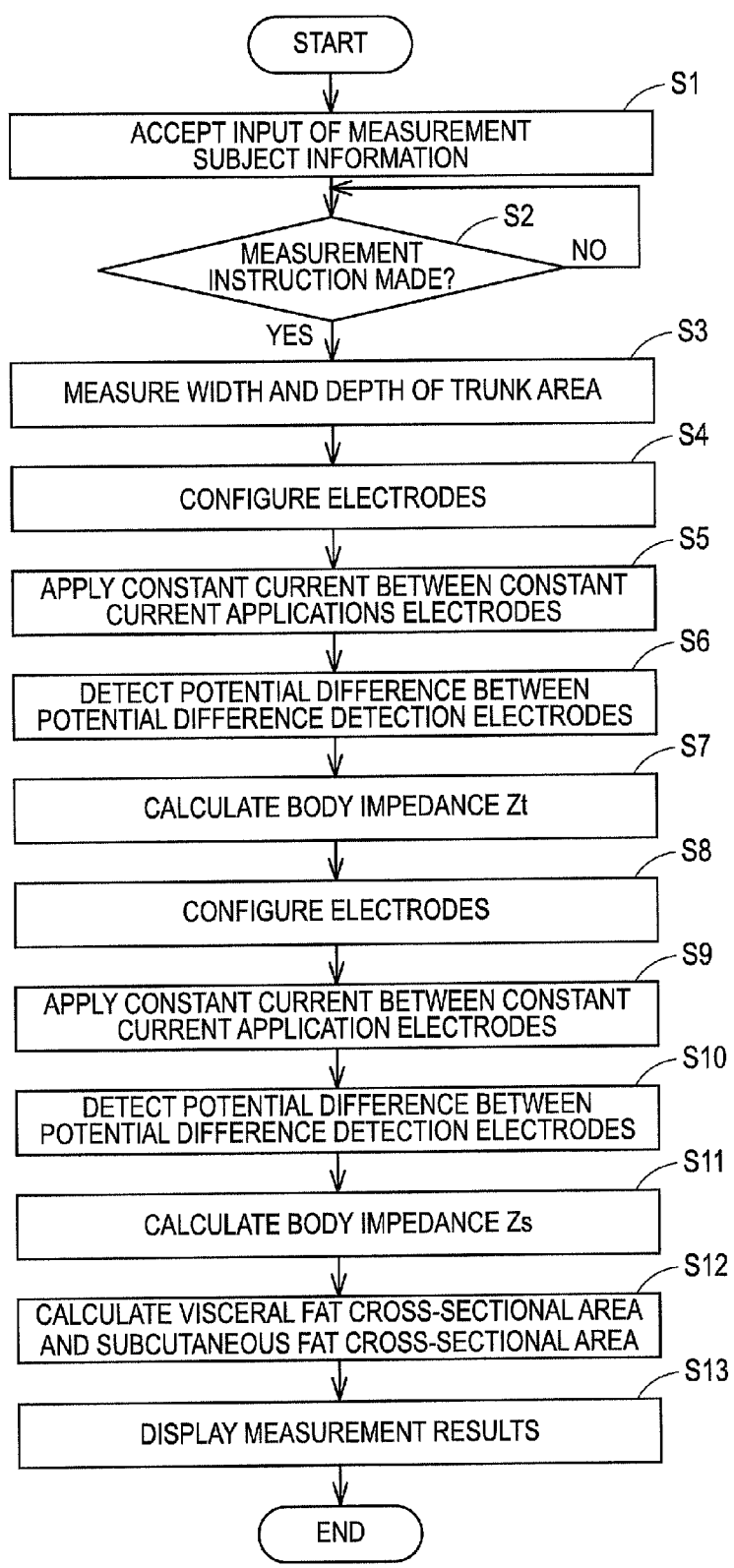
FIG. 11 is a flowchart illustrating a process performed by a control unit in the body fat measurement device according to the first embodiment of the present invention.

FIG. 11 is a flowchart illustrating a process performed by the control unit in the body fat measurement device according to the present embodiment. Next, a sequence of processes executed by the control unit of the body fat measurement device according to the present embodiment will be described with reference to FIG. 11. Note that the processes indicated in the flowchart in FIG. 11 are stored in the memory unit 29 in advance as a program, and a visceral fat cross-sectional area measurement process and a subcutaneous fat cross-sectional area measurement process are realized by the control unit 10 when the control unit 10 including the computation processing unit 11 reads out and executed that program.

As shown in FIG. 11, the control unit 10 first accepts an input of the measurement subject information (step S1). The accepted measurement subject information is temporarily saved in, for example, the memory unit 29.

Next, the control unit 10 determines whether or not there has been an instruction to start the measurement (step S2). The control unit 10 stands by until there has been an instruction to start the measurement (NO in step S2), and advances to the next process in the case where an instruction to start the measurement has been detected (YES in step S2). Note that the instruction to start the measurement is made by the measurement subject depressing the measure button 27a.

Next, the control unit 10 measures the width and depth of the trunk area (step S3). Specifically, the control unit 10 obtains the width 2a and the depth 2b of the trunk area of the measurement subject using the body shape information measurement unit 13, based on signals inputted from the trunk area width detection unit 24A and the trunk area depth detection unit 24B. The obtained width 2a and depth 2b of the trunk area of the measurement subject are temporarily saved in the memory unit 29.

Next, the control unit 10 configures the electrodes (step S4). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1A.

Next, the control unit 10 applies a constant current between the constant current application electrodes (step S5). Specifically, the control unit 10 outputs an instruction to the constant current generation unit 21 for generating the constant current, and based on this, the constant current generation unit 21 applies the constant current $I_A$ generated between the constant current application electrodes as shown in FIG. 1A.

Next, the control unit 10 detects a potential difference between the potential difference detection electrodes (step S6). Specifically, the control unit 10 outputs an instruction to the potential difference detection unit 23 for detecting a potential difference, and based on this, the potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 12.

Next, the control unit 10 calculates the body impedance Zt (step S7). Specifically, the control unit 10 calculates the body impedance Zt using the body impedance measurement unit 12, based on a signal inputted from the potential difference detection unit 23. The calculated body impedance Zt is temporarily saved in the memory unit 29.

Next, the control unit 10 reconfigures the electrodes (step S8). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1B.

Next, the control unit 10 applies a constant current between the constant current application electrodes (step S9). Specifically, the control unit 10 outputs an instruction to the constant current generation unit 21 for generating the constant current, and based on this, the constant current generation unit 21 applies the constant currents $I_{B1}$ and $I_{B2}$ generated between the constant current application electrodes as shown in FIG. 1B.

Next, the control unit 10 detects a potential difference between the potential difference detection electrodes (step S10). Specifically, the control unit 10 outputs an instruction to the potential difference detection unit 23 for detecting a potential difference, and based on this, the potential difference detection unit 23 detects the potential differences $V_{B1}$ and $V_{B2}$ between the potential difference detection electrodes shown in FIG. 1B, and outputs the detected potential differences to the body impedance measurement unit 12.

Next, the control unit 10 calculates the body impedance Zs (step S11). Specifically, the control unit 10 calculates the body impedance Zs using the body impedance measurement unit 12, based on a signal inputted from the potential difference detection unit 23. The calculated body impedance Zs is temporarily saved in the memory unit 29.

Next, the control unit 10 calculates the visceral fat cross-sectional area and the subcutaneous fat cross-sectional area (step S12). Specifically, the control unit 10 calculates the visceral fat cross-sectional area Sx as the visceral fat mass using the visceral fat mass calculation unit 14a and calculates the subcutaneous fat cross-sectional area Sb as the subcutaneous fat mass using the subcutaneous fat mass calculation unit 14b, based on the width 2a and depth 2b of the trunk area detected in step S3, the body impedance Zt calculated in step S7, and the body impedance Zs calculated in step S11. Note that the calculated visceral fat cross-sectional area Sx and subcutaneous fat cross-sectional area Sb are temporarily saved in the memory unit 29.

Then, the control unit 10 displays the measurement results (step S13). Specifically, the control unit 10 outputs, to the display unit 26, an instruction to display the visceral fat cross-sectional area Sx and subcutaneous fat cross-sectional area Sb calculated in step S12, and based on this, the display unit 26 displays those measurement results.

Through this, the body fat measurement device 1A completes the visceral fat cross-sectional area measurement process and the subcutaneous fat cross-sectional area measurement process. Note that a typical value for the body impedance Zt is approximately 5Ω, whereas a typical value for the body impedance Zs is approximately 80Ω.

With the body fat measurement device 1A according to the present embodiment as described thus far, the back area electrodes BU1-BU4 and BL1-BL4, and the hand electrodes HR and HL that serve as the upper limb electrodes, are provided in an exposed state in the fitting unit 100A, which is used to bring the back area electrodes BU1-BU4 and BL1-BL4 into contact with the back area of the measurement subject in a pressurized state. In other words, the back area electrodes BU1-BU4 and BL1-BL4 and the hand electrodes HR and HL are provided so as to be integrated with the fitting unit 100A that is configured as a single unit.

To be more specific, the back area electrodes BU1-BU4 and BL1-BL4 are all provided on the rear area of the frame member 110 of the fitting unit 100A, and the hand electrodes HR and HL are provided on the right side and left side, respectively, of the frame member 110 of the fitting unit 100A, and areas aside from the stated rear area. In other words, the hand electrodes HR and HL are provided at a distance from the back area electrodes BU1-BU4 and BL1-BL4, in an area extending in a continuous manner from the part of the frame member 110 in which the back area electrodes BU1-BU4 and BL1-BL4 are provided, and more specifically, are provided in areas of the frame member 110 that are positioned to the left and right of the measurement subject during the fitted state.

Accordingly, by gripping the fitting unit 100A with the right hand and the left hand, the measurement subject can place the hand electrodes HR and HL in contact with the palm of his/her right hand and the palm of his/her left hand, respectively, and can place the back area electrodes BU1-BU4 and BL1-BL4 provided in the fitting unit 100A in contact with his/her back area surface by pressing the fitting unit 100A to the back area surface while gripping the fitting unit 100A with his/her right hand and left hand.

Here, in the case where a configuration that places the electrodes in contact with the back area surface of the measurement subject is employed without employing the configuration of the body fat measurement device 1A according to the present embodiment as described above, it is difficult to maintain stable contact between the back area electrodes and the measurement subject's back area surface, and thus normally, it is necessary for the measurement subject to lie face up or face down in order to stabilize the contact. However, in the case where the device is configured in this manner, it is extremely difficult for the measurement subject to carry out the measurement by him/herself without help from an assistant or the like, and as a result, the body fat measurement device cannot be used in a household or the like.

However, with the body fat measurement device 1A according to the present embodiment as described above, the back area electrodes BU1-BU4 and BL1-BL4 and the hand electrodes HR and HL are provided integrally with the fitting unit 100A that is configured as a single unit, and it is thus possible to bring the back area electrodes BU1-BU4 and BL1-BL4 into stable contact with the back area surface of the measurement subject through a simple operation and while the measurement subject is standing upright; furthermore, the back area electrodes BU1-BU4 and BL1-BL4 can be kept in stable contact with the back area surface of the measurement subject during the measurement process. Accordingly, with the body fat measurement device 1A according to the present embodiment, the operations required of the measurement subject when measuring the body fat mass can be simplified, and the body fat mass can be measured easily through a simple operation, and furthermore, the measurement subject can carry out the measurement him/herself without help from an assistant or the like.

Furthermore, with the body fat measurement device 1A according to the present embodiment, body fat mass such as the visceral fat mass, the subcutaneous fat mass, and so on can be measured while the back area electrodes BU1-BU4 and BL1-BL4 are placed in contact with the back area surface of the measurement subject, and thus instead of a current being locally applied to the abdominal area, where the subcutaneous fat is relatively thin, a current can be locally applied to the back area, where the subcutaneous fat is relatively thick; thus the body fat mass can be measured with a higher degree of accuracy.

Accordingly, the body fat measurement device 1A according to the present embodiment makes it possible to realize a body fat measurement device capable of measuring body fat mass, such as visceral fat mass and subcutaneous fat mass, easily and accurately within a household or the like. Therefore, using the body fat measurement device 1A makes it possible to obtain such indicators for health management on a daily basis.

Second Embodiment

Figure 12:
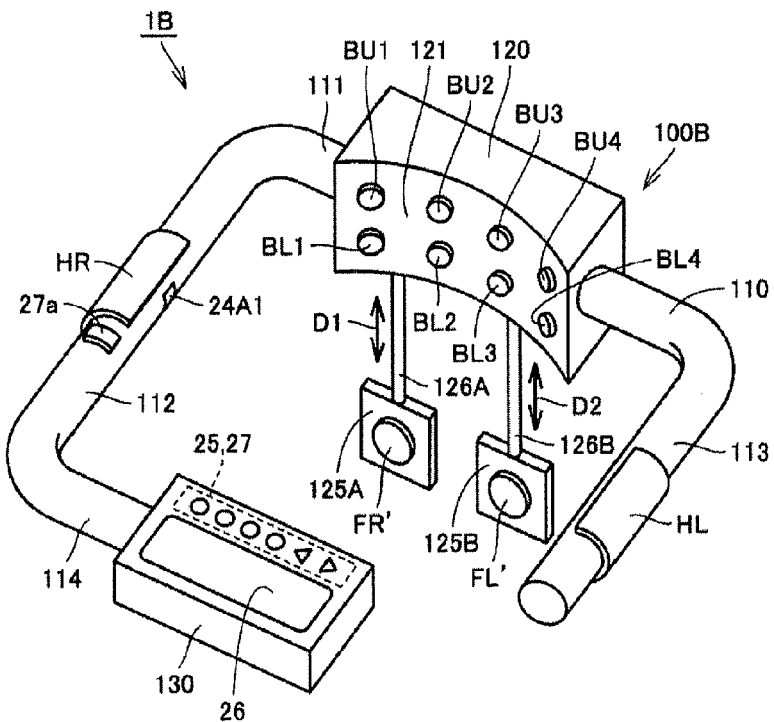
FIG. 12 is a perspective view illustrating a body fat measurement device according to a second embodiment of the present invention.

FIG. 12 is a perspective view illustrating a body fat measurement device according to a second embodiment of the present invention. Next, the structure of the body fat measurement device according to the present embodiment will be described in detail with reference to FIG. 12. Note that the fundamentals of the measurement performed by the body fat measurement device and the computation processes executed by the control unit according to the present embodiment are the same as those of the body fat measurement device according to the aforementioned first embodiment of the present invention.

As shown in FIG. 12, a body fat measurement device 1B according to the present embodiment includes, like the body fat measurement device 1A according to the aforementioned first embodiment of the present invention, a fitting unit 100B having a frame shape capable of being disposed so as to surround the trunk area of the measurement subject in a fitted state. However, unlike the body fat measurement device 1A according to the aforementioned first embodiment of the present invention, the body fat measurement device 1B according to the present embodiment does not include a platform-shaped platform unit on which the measurement subject can stand; instead, electrode pads 125A and 125B, serving as extending unit portions configured so as to be extendable from the fitting unit 100B, are provided.

The electrode pads 125A and 125B have approximate plate shapes, and foot/hip electrodes FL' and FR', serving as lower limb/hip electrodes for making contact with the surface of the respective lower limbs or hips, are provided in an exposed state on the main surfaces of the electrode pads 125A and 125B, respectively. The one ends of connection cables 126A and 126B are attached to upper areas of the electrode pads 125A and 125B, respectively, and the other ends of the connection cables 126A and 126B are anchored to reel members provided within the electrode support member 120. Note that in the fitting unit 100B according to the present embodiment, the electrode support member 120 is configured as a block-shaped member in order to make it possible to dispose the reel members within the electrode support member 120, and the electrode support member 120 is attached in approximately the center of the rear frame portion 111 of the frame member 110.

Through this, the electrode pads 125A and 125B can be extended downward from the fitting unit 100B by pulling the connection cables 126A and 126B, which serve as connection lines, in the direction of arrows D1 and D2 shown in FIG. 12. In other words, by adjusting the extension amount of the connection cables 126A and 126B, the electrode pads 125A and 125B can be attached at desired locations, such as the lower limbs, the hips, and so on of the measurement subject.

With the body fat measurement device 1B according to the present embodiment as described thus far, the same effects as those described in the aforementioned first embodiment of the present invention can be achieved. In addition, with the body fat measurement device 1B according to the present embodiment, the measurement can be carried out in a seated position as well as a standing position, which makes it even easier to measure body fat mass. Furthermore, with the body fat measurement device 1B according to the present embodiment, there is no platform unit, and thus the device configuration can be simplified and the size of the device can be reduced.

Note that pads that attach to the measurement subject's body through suction, through and adhesive, or that are attached by being wrapped around the measurement subject's body using some sort of wrapping member can be used as the electrode pads 125A and 125B; furthermore, pads that are not particularly attached but are anchored by being sandwiched between the measurement subject's body and a seating surface, a floor surface, or the like can be used as the electrode pads 125A and 125B.

Third Embodiment

Figure 13A:
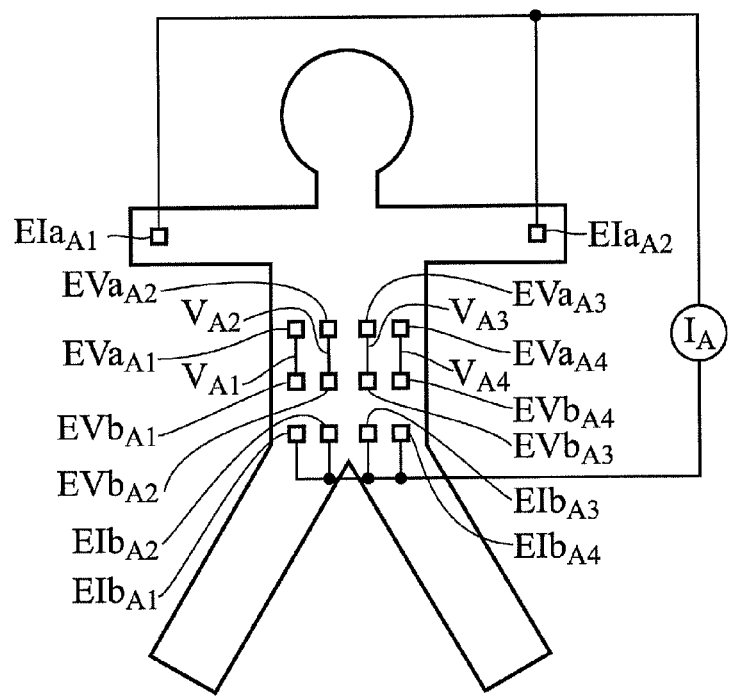
FIG. 13A is a diagram illustrating the fundamentals of measurement performed by a body fat measurement device according to a third embodiment of the present invention.
Figure 13B:
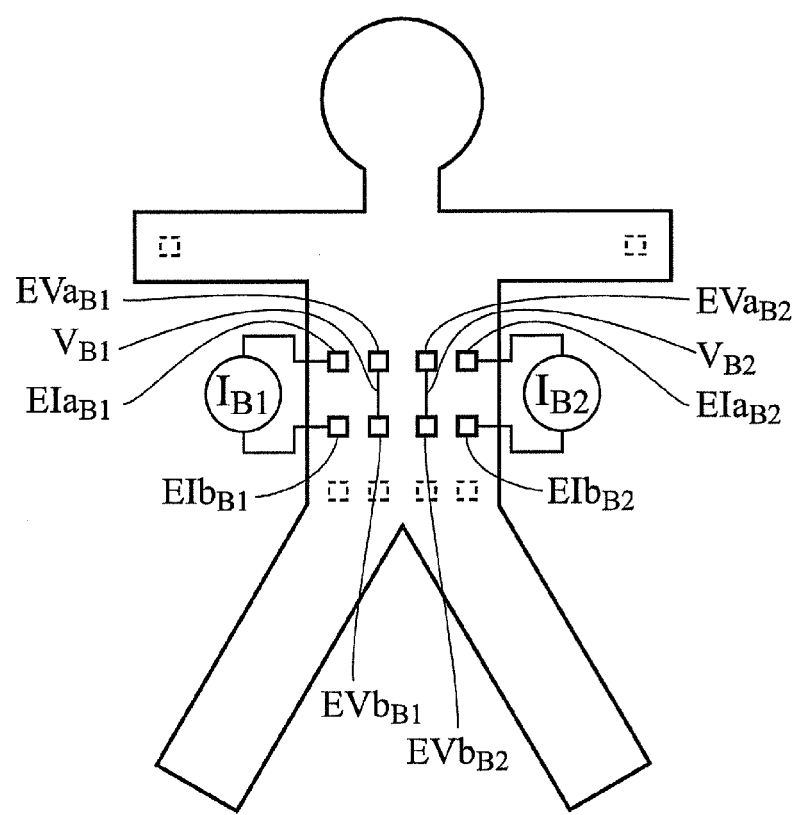
FIG. 13B is a diagram illustrating the fundamentals of measurement performed by the body fat measurement device according to the third embodiment of the present invention.

FIGS. 13A and 13B are diagrams illustrating the fundamentals of measurement performed by a body fat measurement device according to a third embodiment of the present invention. Here, FIG. 13A is a diagram illustrating the placement of electrodes when obtaining a body impedance for the entire trunk area, whereas FIG. 13B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 13A and 13B. Note that FIGS. 13A and 13B both illustrate the measurement subject from the back side thereof.

The fundamentals of the measurement performed by the body fat measurement device according to the present embodiment are also basically the same as the fundamentals of the measurement described in the aforementioned first embodiment of the present invention. However, the positions in which the electrodes used when obtaining the body impedance of the entire trunk area are placed are slightly different from those in the aforementioned first embodiment of the present invention.

Specifically, as shown in FIG. 13A, electrodes $\text{EIa}_{A1}$ and $\text{EIa}_{A2}$ are attached to the surface of the left hand of the measurement subject and the surface of the right hand of the measurement subject, respectively, in order to obtain the body impedance for the entire trunk area. Meanwhile, four pairs of electrodes are attached to the back area surface of the measurement subject, with each pair disposed so as to follow the body axis direction, and with the four pairs arranged in the widthwise direction of the trunk area; furthermore, four electrodes are attached to an area of the back area surface that is closer to the hip area than the contact locations where the stated four pairs of electrodes are placed, with these four electrodes being arranged along the widthwise direction of the trunk area. In other words, as shown in FIG. 13A, a total of twelve electrodes, or electrodes $\text{EVa}_{A1}$, $\text{EVb}_{A1}$, $\text{EVa}_{A2}$, $\text{EVb}_{A2}$, $\text{EVa}_{A3}$, $\text{EVb}_{A3}$, $\text{EVa}_{A4}$, $\text{EVb}_{A4}$, $\text{EIb}_{A1}$, $\text{EIb}_{A2}$, $\text{EIb}_{A3}$, and $\text{EIb}_{A4}$, are attached to the back area surface of the measurement subject.

In this state, a constant current $I_A$ that passes through the trunk area is applied to the measurement subject using the electrodes $\text{EIa}_{A1}$, $\text{EIa}_{A2}$, $\text{EIb}_{A1}$, $\text{EIb}_{A2}$, $\text{EIb}_{A3}$, and $\text{EIb}_{A4}$ attached to both hands and the back area near the hip area, respectively. While the constant current $I_A$ is applied, a potential difference $V_{A1}$ is detected using the pair of electrodes $\text{EVa}_{A1}$ and $\text{EVb}_{A1}$ attached to the back area surface, a potential difference $V_{A2}$ is detected using the pair of electrodes $\text{EVa}_{A2}$ and $\text{EVb}_{A2}$ attached to the back area surface, a potential difference $V_{A3}$ is detected using the pair of electrodes $\text{EVa}_{A3}$ and $\text{EVb}_{A3}$ attached to the back area surface, and a potential difference $V_{A4}$ is detected using the pair of electrodes $\text{EVa}_{A4}$ and $\text{EVb}_{A4}$ attached to the back area surface.

With a body fat measurement device 1C according to the present embodiment, a body impedance Zt of the entire trunk area is calculated from the potential differences $V_{A1}$, $V_{A2}$, $V_{A3}$, and $V_{A4}$ detected in this manner. Note that the placement of electrodes, the constant current application, and the potential difference detection for obtaining the body impedance Zs of the surface layer area on the back area of the trunk area are, as shown in FIG. 13B, all the same as those in the aforementioned first embodiment of the present invention.

Figure 14:
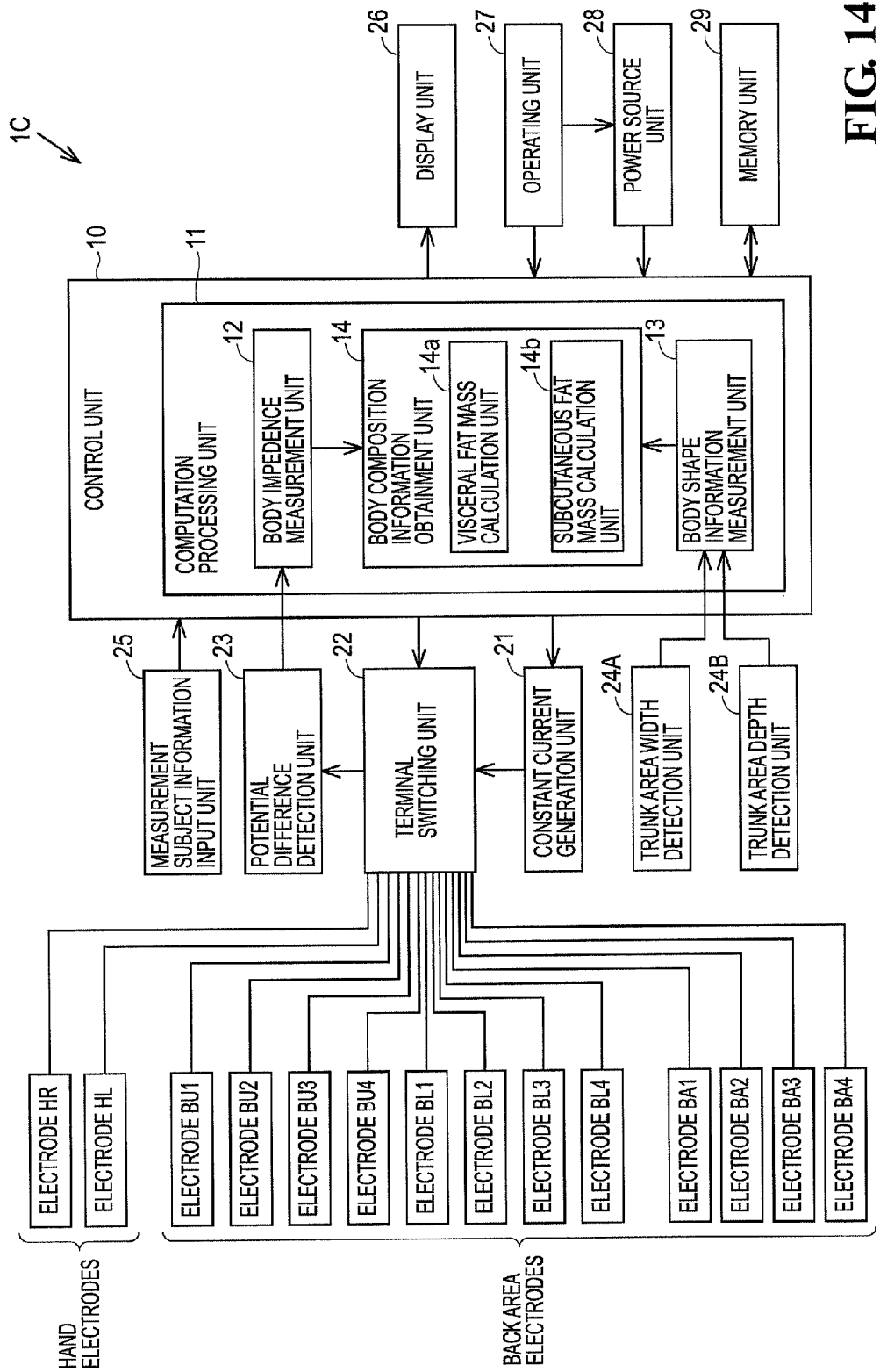
FIG. 14 is a diagram illustrating the functional block configuration of the body fat measurement device according to the third embodiment of the present invention.

FIG. 14 is a diagram illustrating the functional block configuration of the body fat measurement device according to the present embodiment. Next, the functional block configuration of the body fat measurement device according to the present embodiment will be described with reference to FIG. 14.

As shown in FIG. 14, the body fat measurement device 1C according to the present embodiment has a similar configuration as the body fat measurement device 1A according to the aforementioned first embodiment of the present invention, but differs slightly in terms of the configuration of the multiple electrodes connected to the terminal switching unit 22. In other words, the body fat measurement device 1C according to the present embodiment includes electrodes HR, HL, BU1-BU4, BL1-BL4, and BA1-BA4 as the multiple electrodes.

The aforementioned multiple electrodes include: hand electrodes HR and HL serving as upper limb electrodes placed in contact with surfaces of the upper limbs of the measurement subject; and back area electrodes BU1-BU4, BL1-BL4, and BA1-BA4 placed in contact with the back area surface of the measurement subject. Of these, the hand electrodes HR and HL are placed in contact with the palms of the measurement subject's hands. Meanwhile, as shown in FIGS. 13A and 13B, the back area electrodes BU1-BU4, BL1-BL4, and BA1-BA4 are arranged in rows and placed in contact with the back area surface of the measurement subject. Note that the hand electrodes HR and HL and the back area electrodes BU1-BU4, BL1-BL4, and BA1-BA4 are all electrically connected to the terminal switching unit 22 described above.

Figure 15:
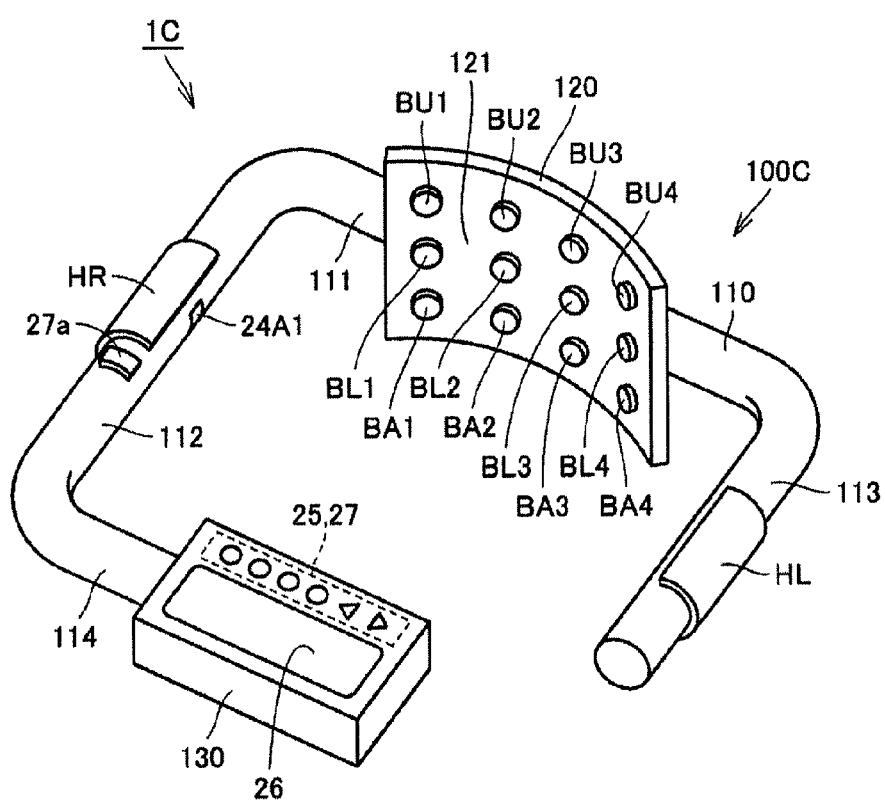
FIG. 15 is a perspective view illustrating the body fat measurement device according to the third embodiment of the present invention.

FIG. 15 is a perspective view illustrating the body fat measurement device according to the present embodiment. Next, the structure of the body fat measurement device according to the present embodiment will be described in detail with reference to FIG. 15.

As shown in FIG. 15, the body fat measurement device 1C according to the present embodiment includes, like the body fat measurement device 1A according to the aforementioned first embodiment of the present invention, a fitting unit 100C having a frame shape capable of being disposed so as to surround the trunk area of the measurement subject in a fitted state. However, unlike the body fat measurement device 1A according to the aforementioned first embodiment of the present invention, the body fat measurement device 1C according to the present embodiment does not include a platform-shaped platform unit on which the measurement subject can stand. Instead, with the body fat measurement device 1C according to the present embodiment, the back area electrodes BA1-BA4 are further provided on the electrode support member 120 attached to the frame member 110.

To be more specific, the electrode support member 120, which is configured of a curved plate, extends further downward than in the aforementioned first embodiment of the present invention, and the back area electrodes BA1-BA4 are provided on the front surface 121 of the area of the electrode support member 120 that has been extended. Here, the back area electrodes BA1-BA4 are provided so that all the electrodes are exposed on the front surface 121 of the electrode support member 120, and preferably, the back area electrodes BA1-BA4 protrude slightly from the front surface 121 of the electrode support member 120. Through this, the back area electrodes BA1-BA4 are, like the back area electrodes BU1-BU4 and BL1-BL4, placed in contact with the back area surface of the measurement subject during the fitted state.

With the body fat measurement device 1C according to the present embodiment as described thus far, the same effects as those described in the aforementioned first embodiment of the present invention can be achieved. In addition, with the body fat measurement device 1C according to the present embodiment, the measurement can be carried out in a seated position as well as a standing position, which makes it even easier to measure body fat mass. Furthermore, with the body fat measurement device 1C according to the present embodiment, there is no platform unit, and thus the device configuration can be simplified and the size of the device can be reduced.

Fourth Embodiment

Figure 16:
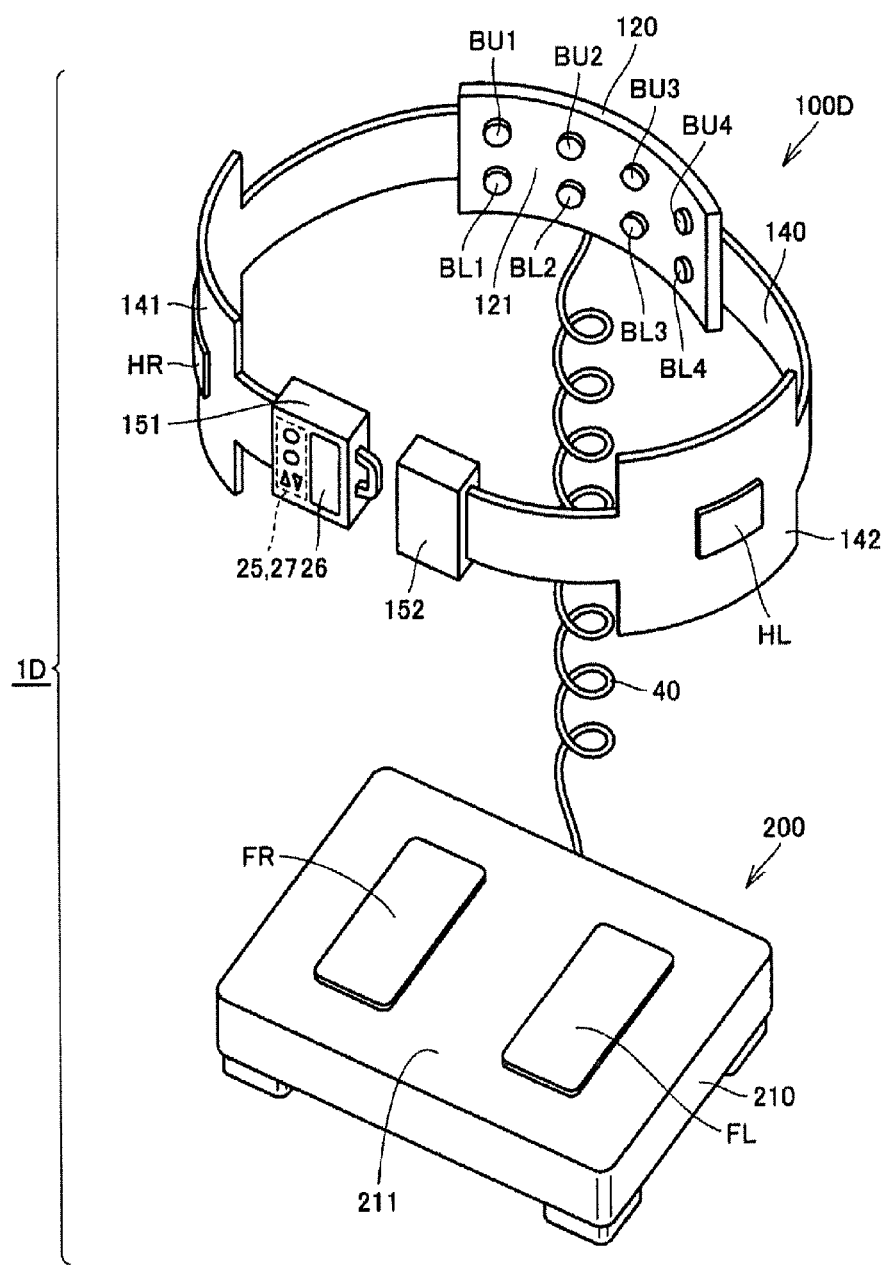
FIG. 16 is a perspective view illustrating the body fat measurement device according to a fourth embodiment of the present invention.

FIG. 16 is a perspective view illustrating a body fat measurement device according to a fourth embodiment of the present invention. Next, the structure of the body fat measurement device according to the present embodiment will be described in detail with reference to FIG. 16. Note that the fundamentals of the measurement performed by the body fat measurement device and the computation processes executed by the control unit according to the present embodiment are the same as those of the body fat measurement device according to the aforementioned first embodiment of the present invention.

As shown in FIG. 16, a body fat measurement device 1D according to the present embodiment includes a fitting unit and a platform unit, in the same manner as the body fat measurement device 1A according to the aforementioned first embodiment of the present invention. However, the body fat measurement device 1D according to the present embodiment differs from the body fat measurement device 1A according to the aforementioned first embodiment of the present invention in terms of the structure of the fitting unit.

Specifically, as shown in FIG. 16, a fitting unit 100D is shaped as a belt that can be wrapped around the trunk area of the measurement subject in a fitted state, which will be described later. The fitting unit 100D includes a belt member 140 and buckle portions 151 and 152, and the buckle portions 151 and 152 are attached to the respective ends of the belt member 140 in the lengthwise direction thereof. The buckle portions 151 and 152 are portions for anchoring the belt member 140 in a looped stated by engaging both ends of the belt member 140. Meanwhile, the measurement subject information input unit 25, the display unit 26, and the operating unit 27 including the power button are provided on the front surface of the one buckle portion 151.

The electrode support member 120 is disposed in approximately the center of the rear area of the belt member 140 so as to protrude inward. The electrode support member 120 is configured of a curved plate that is bent so that both ends thereof are positioned forward and the center thereof is positioned rearward. The aforementioned back area electrodes BU1-BU4 and BL1-BL4 are provided so as to be exposed on a front surface 121 of the electrode support member 120, and preferably, the back area electrodes BU1-BU4 and BL1-BL4 protrude slightly from the front surface 121 of the electrode support member 120. Here, the electrode support member 120 is positioned and attached on the inner circumferential surface of the rear area of the belt member 140 so that surfaces of the back area electrodes BU1-BU4 and BL1-BL4 that make contact with the back area surface of the measurement subject face forward during the fitted state, which will be mentioned later.

Meanwhile, the hand electrode HR is provided on the right-front of the outer circumferential surface of the belt member 140. The hand electrode HR is positioned and exposed on the outer circumferential surface of the belt member 140, and preferably, the hand electrode HR protrudes slightly from the outer circumferential surface of the belt member 140. Here, the area of the belt member 140 on which the hand electrode HR is provided is formed as a smoothly curving surface, so that the palm of the measurement subject's right hand can make contact with the hand electrode HR by being placed thereon in the fitted state as described later, without gripping the belt member 140.

A widened area 141, formed so as to be wider than the other areas of the belt member 140, is provided in the area of the belt member 140 on which the hand electrode HR is provided, and the hand electrode HR is disposed in approximately the center of the widened area 141. Note that the widened area 141 is for preventing the palm of the measurement subject's right hand from coming into contact with the abdominal area and causing a short-circuit at that area during the fitted state, which will be described later.

Meanwhile, the hand electrode HL is provided on the left-front of the outer circumferential surface of the belt member 140. The hand electrode HL is positioned and exposed on the outer circumferential surface of the belt member 140, and preferably, the hand electrode HL protrudes slightly from the outer circumferential surface of the belt member 140. Here, the area of the belt member 140 on which the hand electrode HL is provided is formed as a smoothly curving surface, so that the palm of the measurement subject's left hand can make contact with the hand electrode HL by being placed thereon in the fitted state as described later, without gripping the belt member 140.

A widened area 142, formed so as to be wider than the other areas of the belt member 140, is provided in the area of the belt member 140 on which the hand electrode HL is provided, and the hand electrode HL is disposed in approximately the center of the widened area 142. Note that the widened area 142 is for preventing the palm of the measurement subject's left hand from coming into contact with the abdominal area and causing a short-circuit at that area during the fitted state, which will be described later.

Note that a fitting length adjustment mechanism may be provided in the fitting unit 100D. By employing such a configuration, the fitting unit 100D can be wrapped around the measurement subject's trunk area having adjusted the belt member 140 to a fitting length that is suited to the circumferential length of the measurement subject's trunk area. In addition, in the case where the fitting length adjustment mechanism is provided in the belt member 140, a fitting length detection mechanism may further be provided. By employing such a configuration, the actual circumferential length of the measurement subject's trunk area can be measured, which can then be used as the measurement subject information when measuring the body fat mass.

Figure 17:
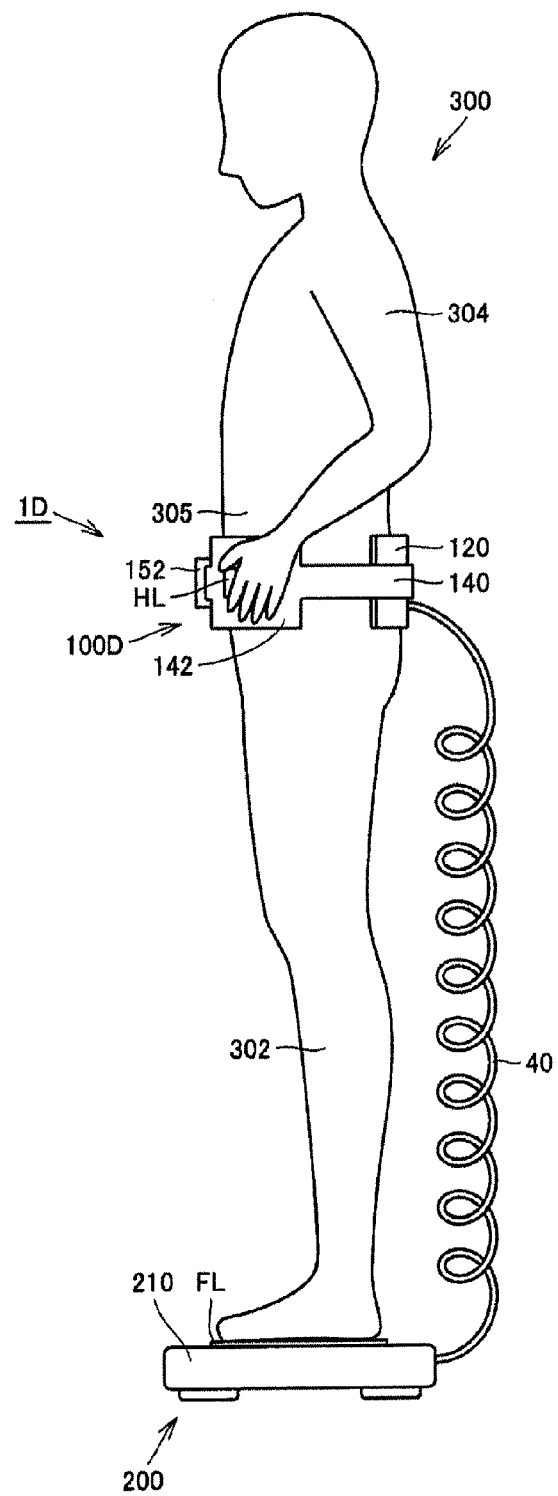
FIG. 17 is a diagram illustrating the body fat measurement device according to the fourth embodiment of the present invention in a fitted state.

FIG. 17 is a diagram illustrating the fitting unit of the body fat measurement device according to the present embodiment in the fitted state. Next, the fitted state of the fitting unit in the body fat measurement device according to the present embodiment will be described with reference to FIG. 17.

As shown in FIG. 17, when measuring body fat mass using the body fat measurement device 1D according to the present embodiment, the measurement subject 300 wraps the fitting unit 100D around his/her trunk area 305 in the circumferential direction, and in that state, stands on the platform unit 200. At this time, the measurement subject 300 adjusts the wrapped position of the fitting unit 100D so that the front surface 121 of the electrode support member 120 provided on the fitting unit 100D is pressed against the back area surface (and more specifically, against the surface of the lower area of the back), brings the sole of the right foot 301 into contact with the foot electrode FR provided on the platform unit 200, and bring the sole of the left foot 302 into contact with the foot electrode FL provided on the platform unit 200.

Next, the measurement subject 300 places the palms of his/her right hand 303 and left hand 304 on the hand electrodes HR and HL, respectively, located on the right-front and left-front of the fitting unit 100D. At this time, the measurement subject 300 brings the palm of his/her right hand 303 into contact with the hand electrode HR provided in the fitting unit 100D, and brings the palm of his/her left hand 304 into contact with the hand electrode HL provided in the fitting unit 100D.

As a result, the fitting unit 100D enters the fitted state shown in FIG. 17, and the measurement of body fat mass can be started. Here, in order to start the measurement of the body fat mass, the measurement subject 300 may depress the measure button provided in the buckle portion 151 using the thumb of his/her right hand 303.

With the body fat measurement device 1D according to the present embodiment as described thus far, the back area electrodes BU1-BU4 and BL1-BL4, and the hand electrodes HR and HL that serve as the upper limb electrodes, are provided in an exposed state in the fitting unit 100D, which is used to bring the back area electrodes BU1-BU4 and BL1-BL4 into contact with the back area of the measurement subject in a pressurized state. In other words, the back area electrodes BU1-BU4 and BL1-BL4 and the hand electrodes HR and HL are provided so as to be integrated with the fitting unit 100D that is configured as a single unit.

To describe in further detail, the back area electrodes BU1-BU4 and BL1-BL4 are all provided in a rear area of the belt member 140 of the fitting unit 100D, and the hand electrodes HR and HL are provided on the right-front and the left-front, respectively, in areas outside of the rear area of the belt member 140 of the fitting unit 100D. In other words, the hand electrodes HR and HL are provided at a distance from the back area electrodes BU1-BU4 and BL1-BL4, in an area extending in a continuous manner from the part of the belt member 140 in which the back area electrodes BU1-BU4 and BL1-BL4 are provided, and more specifically, are provided in areas of the belt member 140 that are positioned to the left and right in front of the measurement subject during the fitted state.

Accordingly, by wrapping the fitting unit 100D around the trunk area, the back area electrodes BU1-BU4 and BL1-BL4 provided in the fitting unit 100D can be placed in contact with the back area surface in a pressurized state, and by placing the right hand and left hand in predetermined positions of the fitting unit 100D, the palms of the right hand and left hand can be placed in contact with the hand electrodes HR and HL, respectively, provided in the fitting unit 100D, without gripping anything.

Here, in the case where a configuration that places the electrodes in contact with the back area surface of the measurement subject is employed without employing the configuration of the body fat measurement device 1D according to the present embodiment as described above, it is difficult to maintain stable contact between the back area electrodes and the measurement subject's back area surface, and thus normally, it is necessary for the measurement subject to lie face up or face down in order to stabilize the contact. However, in the case where the device is configured in this manner, it is extremely difficult for the measurement subject to carry out the measurement by him/herself without help from an assistant or the like, and as a result, the body fat measurement device cannot be used in a household or the like.

However, with the body fat measurement device 1D according to the present embodiment as described above, the back area electrodes BU1-BU4 and BL1-BL4 and the hand electrodes HR and HL are provided integrally with the fitting unit 100D that is configured as a single unit, and it is thus possible to bring the back area electrodes BU1-BU4 and BL1-BL4 into stable contact with the back area surface of the measurement subject through a simple operation and while the measurement subject is standing upright; furthermore, the back area electrodes BU1-BU4 and BL1-BL4 can be kept in stable contact with the back area surface of the measurement subject during the measurement process. Accordingly, with the body fat measurement device 1D according to the present embodiment, the operations required of the measurement subject when measuring the body fat mass can be simplified, and the body fat mass can be measured easily through a simple operation, and furthermore, the measurement subject can carry out the measurement him/herself without help from an assistant or the like.

Furthermore, with the body fat measurement device 1D according to the present embodiment, body fat mass such as the visceral fat mass, the subcutaneous fat mass, and so on can be measured while the back area electrodes BU1-BU4 and BL1-BL4 are placed in contact with the back area surface of the measurement subject, and thus instead of a current being locally applied to the abdominal area, where the subcutaneous fat is relatively thin, a current can be locally applied to the back area, where the subcutaneous fat is relatively thick; thus the body fat mass can be measured with a higher degree of accuracy.

Accordingly, the body fat measurement device 1D according to the present embodiment makes it possible to realize a body fat measurement device capable of measuring body fat mass, such as visceral fat mass and subcutaneous fat mass, easily and accurately within a household or the like. Therefore, using the body fat measurement device 1D makes it possible to obtain such indicators for health management on a daily basis.

Figure 18:
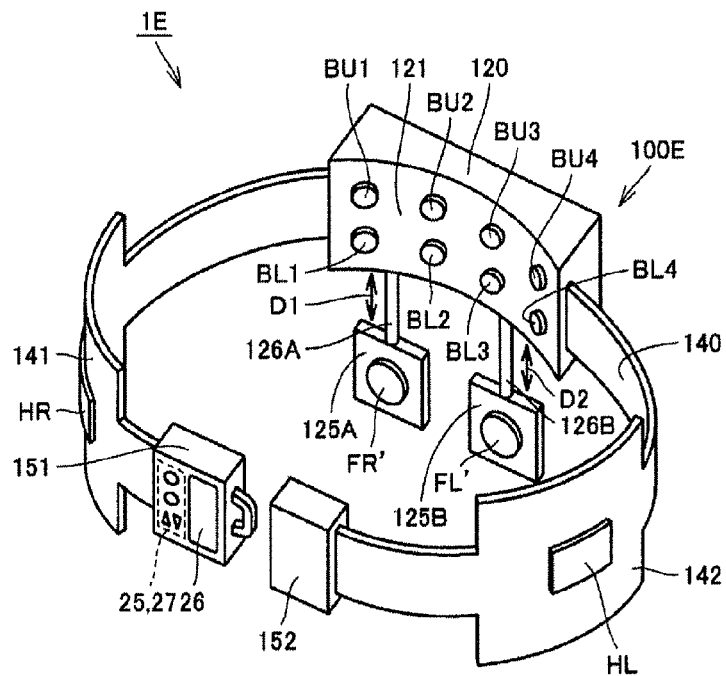
FIG. 18 is a perspective view illustrating a body fat measurement device according to a first variation on the fourth embodiment of the present invention.
Figure 19:
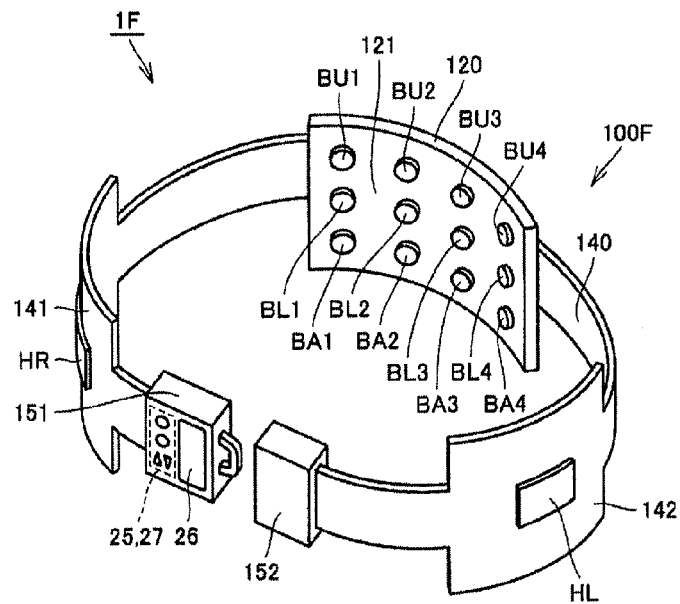
FIG. 19 is a perspective view illustrating a body fat measurement device according to a second variation on the fourth embodiment of the present invention.

FIGS. 18 and 19 are perspective view illustrating body fat measurement devices according to first and second variations, respectively, on the present embodiment. Next, the structures of the body fat measurement devices according to the first and second variations on the present embodiment will be described in detail with reference to FIGS. 18 and 19.

As shown in FIG. 18, a body fat measurement device 1E according to the first variation eliminates the platform unit by adding, to the body fat measurement device 1D according to the present embodiment, the electrode pads 125A and 125B serving as extending unit portions that are provided in the body fat measurement device 1B according to the aforementioned second embodiment of the present invention. Specifically, the electrode pads 125A and 125B are connected, so as to be capable of extending, via the connection cables 126A and 126B to the block-shaped electrode support member 120, which is attached to a rear area of the belt member 140 in a fitting unit 100E; the foot/hip electrodes FL' and FR', serving as lower limb/hip electrodes for making contact with the surface of the respective lower limbs or hips, are provided in an exposed state on the main surfaces of the electrode pads 125A and 125B, respectively.

Even when such a configuration is employed, the same effects as the effects described above in the present embodiment can be achieved. Furthermore, with the body fat measurement device 1E according to the present variation, the measurement can be carried out in a seated position as well as in a standing position, and the body fat mass can be measured even more easily. Furthermore, with the body fat measurement device 1E according to the present embodiment, there is no platform unit, and thus the device configuration can be simplified and the size of the device can be reduced.

As shown in FIG. 19, a body fat measurement device 1F according to the second variation eliminates the platform unit by adding, to the body fat measurement device 1D according to the present embodiment, the electrode support member that is provided in the body fat measurement device 1C according to the aforementioned third embodiment of the present invention. Specifically, the back area electrodes BA1-BA4 are provided in an exposed state on the front surface 121 of the electrode support member 120, which is configured of a curved plate that is attached to a rear area of the belt member 140 in a fitting unit 100F; accordingly, the back area electrodes BA1-BA4 can be placed in contact with the back area surface of the measurement subject during the fitted state, in the same manner as the back area electrodes BU1-BU4 and BL1-BL4.

Even when such a configuration is employed, the same effects as the effects described above in the present embodiment can be achieved. Furthermore, with the body fat measurement device 1F according to the present variation, the measurement can be carried out in a seated position as well as in a standing position, and the body fat mass can be measured even more easily. Furthermore, with the body fat measurement device 1F according to the present embodiment, there is no platform unit, and thus the device configuration can be simplified and the size of the device can be reduced.

Of the first through fourth embodiments and variations thereon according to the present invention as described thus far, the first through third embodiments of the present invention have described examples in which the hand electrodes HR and HL are provided on the right-side frame portion 112 and the left-side frame portion 113, respectively, of the frame member 110 in the fitting units 100A through 100C; however, it should be noted that the hand electrodes HR and HL may be provided on the front frame portion 114 of the frame member 110 instead.

In addition, although the aforementioned first through third embodiments of the present invention have described examples in which part of the frame member 110 in the fitting units 100A through 100C is not continuous, the configuration may be such that the shape is continuous.

In addition, although the aforementioned first through third embodiments of the present invention have described examples in which the frame member 110 of the fitting units 100A through 100C has a frame-shaped outer shape that is approximately rectangular when viewed from above, the frame member 110 may be configured having a different shape, such as a ring shape, a U shape, a C shape, or the like.

In addition, although the aforementioned fourth embodiment and variations thereon according to the present invention describe an example in which the hand electrodes HR and HL are provided on the outer circumferential surface of the right-front and left-front of the belt member 140 in the fitting units 100D-100F, the hand electrodes HR and HL may be provided in any positions as long as the positions are between the side areas (that is, the right side and the left side) and the front area of the outer circumferential surface of the belt member 140.

In addition, although the aforementioned fourth embodiment and the variations thereon according to the present invention describe examples in which the area of the belt member 140 in the fitting units 100D-100F in which the hand electrodes HR and HL are provided is configured as a smooth curved surface, this area may have any shape, such as a plate shape, as long as the shape enables the palm of the right hand and the palm of the left hand to come into contact with the hand electrodes HR and HL without the right hand or the left hand gripping those areas by being placed thereon.

In addition, in the aforementioned first through fourth embodiments of the present invention, the configuration includes the platform unit 200, and thus the platform unit 200 may be provided with a body weight measurement function. In other words, the configuration may be such that a load cell or the like that serves as a body weight measurement unit for detecting a load on the platform unit 200 is provided, which enables the weight of the measurement subject standing on the platform unit 200 to be measured by the body weight measurement unit. In this case, if the configuration is such that body weight information measured by the body weight measurement unit provided in the platform unit 200 is inputted into the control unit 10, the actual measured body weight of the target subject can be used as measurement subject information in the various types of computation processes.

In addition, although the aforementioned first through fourth embodiments, and the variations thereon, of the present invention describe examples in which the computation processes are configured so as to calculate the visceral fat cross-sectional area as the visceral fat mass and the subcutaneous fat cross-sectional area as the subcutaneous fat mass, the computation processes may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

In addition, although the aforementioned first through fourth embodiments, and the variations thereon, of the present invention describe examples in which the configuration is such that both the visceral fat cross-sectional area and the subcutaneous fat cross-sectional area are calculated and displayed, the configuration may be such that only one of these indicators is displayed, or that only the subcutaneous fat cross-sectional area is calculated and displayed. Furthermore, the configuration may be such that various types of body composition information aside from the visceral fat cross-sectional area and the subcutaneous fat cross-sectional area (for example, the body fat mass, area-by-area fat mass, fat-free mass, and so on) are calculated and displayed.

In this manner, the embodiments and variations disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE SIGNS LIST 1A-1F body fat measurement device
10 control unit
11 computation processing unit
12 body impedance measurement unit
13 body shape information measurement unit
14 body composition information obtainment unit
14a visceral fat mass calculation unit
14b subcutaneous fat mass calculation unit
21 constant current generation unit
22 terminal switching unit
23 potential difference detection unit
24A trunk area width detection unit
24B trunk area depth detection unit
24A1, 24A2, 24B1 detection window portion
25 measurement subject information input unit
26 display unit
27 operating unit
27a measure button
28 power source unit
29 memory unit
40 connection cable
100A-100F fitting unit
110 frame member
111 rear frame portion
112 right-side frame portion
113 left-side frame portion
114 front frame portion
115 connection portion
120 electrode support member
121 front surface
125A, 125B electrode pad
126A, 126B connection cable
130 display unit portion
140 belt member
141, 142 widened area
151, 152 buckle portion
00 platform unit
210 platform portion
211 top surface
220 support portion
300 measurement subject
301 right foot
302 left foot
303 right hand
304 left hand
305 trunk area
HR, HL hand electrode
BU1-BU4, BL1-BL4, BA1-BA4 back area electrode
FR, FL foot electrode
FL', FR' foot/hip electrode

The invention claimed is:

1. A body fat measurement device for measuring a body fat mass of a subject's body having an abdomen surface, a back surface opposite to the abdomen surface, hands and feet, said device comprising:

multiple electrode arrangements for making contact with predetermined areas of a surface of the subject's body;

a body impedance measurement unit configured to perform a measurement of a body impedance of the subject's body using the multiple electrode arrangements; and a body fat mass calculation unit configured to perform the measurement of the body fat mass based on the body impedance measured by the body impedance measurement unit, wherein the multiple electrode arrangements comprise at least a back area electrode arrangement for making contact with the back surface of the subject, and an upper limb electrode arrangement for making contact with a surface of at least one of the hands of the subject;

the body fat measurement device further comprising a fitting unit for bringing the back area electrode arrangement into contact with the back surface of the subject in a pressurized state, when the fitting unit is in a fitted state;

the fitting unit including a frame member comprising a rear frame portion, a first side frame portion extending from one end of the rear frame portion, a second side frame portion extending from an other end of the rear frame portion, and a front frame portion extending from the first side frame portion;

wherein the back area electrode arrangement is provided on the rear frame portion so that the back area electrode arrangement contacts with the back surface of the subject when in the fitted state;

wherein the upper limb electrode arrangement is provided at least on any one of the first side frame, the second side frame, or the front frame; and wherein the rear frame portion and the front frame portion are spaced a predetermined distance so that the front frame portion and the subject's abdomen surface do not come in contact when in the fitted state, the body fat measurement device further comprising a display unit configured to perform the display of the body fat mass calculated by the body fat mass calculation unit, said display unit being provided on the front frame portion of the frame member so as to face upward when in the fitted state.

2. The body fat measurement device according to claim 1, wherein the multiple electrode arrangements further comprise a lower limb electrode arrangement for making contact with a surface of at least one of the feet of the subject;

wherein the body fat measurement device further comprises a platform unit for bringing the lower limb electrode arrangement into contact with soles of the subject's feet when the subject stands on the platform unit; and wherein the lower limb electrode arrangement is provided on a top surface of the platform unit in an exposed state.

3. The body fat measurement device according to claim 2, wherein the platform unit includes a body weight measurement unit that measures the weight of the subject.

4. The body fat measurement device according to claim 1, for further measuring the fat mass of the subject's body further having a hip, wherein the multiple electrode arrangements further include a lower limb/hip electrode arrangement for making contact with surfaces of the subject's feet or a hip area;

wherein the fitting unit includes extending unit portions for bringing the lower limb/hip electrode arrangement into contact with the surfaces of the feet or hip area by being pulled out from the fitting unit via connection lines; and the lower limb/hip electrode arrangement is provided on a surface of each of the extending unit portions in an exposed state.

5. The body fat measurement device according to claim 1, wherein the body fat mass calculation unit includes at least one of a visceral fat mass calculation unit configured to perform the measurement of the visceral fat mass of the subject and a subcutaneous fat mass calculation unit configured to perform the measurement of the subcutaneous fat mass of the subject.

6. The body fat measurement device according to claim 1, wherein an operating unit through which the subject makes operations is further provided in the front frame portion of the frame member.

* * * * *